United States Patent
Bydlon et al.

(10) Patent No.: US 11,547,318 B2
(45) Date of Patent: Jan. 10, 2023

(54) MEDICAL NAVIGATION SYSTEM USING SHAPE-SENSING DEVICE AND METHOD OF OPERATION THEREOF

(71) Applicant: KONINKLIJKE PHILIPS N.V., Eindhoven (NL)

(72) Inventors: Torre Michelle Bydlon, Melrose, MA (US); Paul Thienphrapa, Cambridge, MA (US); Molly Lara Flexman, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 791 days.

(21) Appl. No.: 16/475,695

(22) PCT Filed: Jan. 3, 2018

(86) PCT No.: PCT/EP2018/050152
§ 371 (c)(1),
(2) Date: Jul. 3, 2019

(87) PCT Pub. No.: WO2018/127522
PCT Pub. Date: Jul. 12, 2018

(65) Prior Publication Data
US 2019/0374130 A1    Dec. 12, 2019

Related U.S. Application Data

(60) Provisional application No. 62/441,598, filed on Jan. 3, 2017.

(51) Int. Cl.
*A61B 5/06* (2006.01)
*A61B 34/30* (2016.01)
(Continued)

(52) U.S. Cl.
CPC ............ *A61B 5/066* (2013.01); *A61B 1/2676* (2013.01); *A61B 34/30* (2016.02);
(Continued)

(58) Field of Classification Search
CPC ..... A61B 5/066; A61B 5/0084; A61B 5/6852; A61B 1/2676; A61B 34/30;
(Continued)

(56) References Cited

U.S. PATENT DOCUMENTS

| 8,050,523 B2 | 11/2011 | Younge |
| 2008/0118135 A1* | 5/2008 | Averbuch ............... A61B 34/10 |
| | | 382/131 |

(Continued)

FOREIGN PATENT DOCUMENTS

| CN | 102949240 | 3/2013 |
| WO | 2011/101754 | 8/2011 |

(Continued)

OTHER PUBLICATIONS

International Search Report and Written Opinion dated Jun. 6, 2018 for International Application No. PCT/EP2018/050152 Filed Jan. 3, 2018.

(Continued)

*Primary Examiner* — Sean D Mattson

(57) ABSTRACT

A medical navigation system including a controller configured to: generate a three-dimensional (3D) volume based upon acquired image information of a region of interest (ROI), determine a reference path (RP) to an object-of-interest (OOI) situated within the ROI, the RP defining an on-road path (ONP) through at least one natural pathway of an organ subject to cyclical motion and an adjacent off-road path (ORP) through tissue of the organ leading to the OOI, and an exit point situated between the ONP and the ORP, query an SSD within the at least one natural pathway to (Continued)

obtain SSDI, determine a shape and a pose of one or more portions of the SSD in accordance with the SSDI, calculate an error between the RP and the determined shape and pose of the SSD, and/or determine when or where to exit a wall of the natural pathway and begin the ORP based upon the calculated error.

18 Claims, 8 Drawing Sheets

(51) Int. Cl.
    *A61B 1/267*     (2006.01)
    *A61B 17/00*     (2006.01)
    *A61B 34/20*     (2016.01)
    *A61B 34/10*     (2016.01)

(52) U.S. Cl.
    CPC .............. *A61B 2017/00699* (2013.01); *A61B 2017/00703* (2013.01); *A61B 2034/107* (2016.02); *A61B 2034/2061* (2016.02); *A61B 2034/301* (2016.02); *A61B 2034/303* (2016.02)

(58) Field of Classification Search
    CPC .......... A61B 2017/00699; A61B 2017/00703; A61B 2017/00292; A61B 2017/00809; A61B 2034/107; A61B 2034/2061; A61B 2034/301; A61B 2034/303; A61B 2018/00541; A61B 2018/00982; A61B 10/04; A61B 6/03; A61B 6/12; A61B 6/466; A61B 6/487; A61B 6/5235; A61B 6/5264; A61B 8/12; A61B 8/1492; G06T 2207/30021; G06T 2207/30061

See application file for complete search history.

(56) References Cited

U.S. PATENT DOCUMENTS

| | | | |
|---|---|---|---|
| 2012/0302878 A1* | 11/2012 | Liu | ........................ A61B 5/064 600/424 |
| 2013/0109957 A1 | 5/2013 | Hooft | |
| 2013/0204124 A1* | 8/2013 | Duindam | ........... A61B 10/0233 604/272 |
| 2014/0039306 A1 | 2/2014 | Klinder | |
| 2015/0012011 A1 | 1/2015 | Trovato | |
| 2015/0265368 A1* | 9/2015 | Chopra | ................... A61B 34/20 600/587 |
| 2016/0000414 A1 | 1/2016 | Brown | |
| 2017/0265952 A1* | 9/2017 | Donhowe | .............. A61B 34/35 |

FOREIGN PATENT DOCUMENTS

| | | |
|---|---|---|
| WO | 2013/031637 | 3/2013 |
| WO | 2015/049142 | 4/2015 |
| WO | 2016/018648 | 2/2016 |
| WO | 2017/055620 | 4/2017 |

OTHER PUBLICATIONS

Chen, et al: "The effect of respiratory motion on pulmonary nodule location during electromagnetic navigation bronchoscopy", CHEST, 2014, pp. 1275-1281.

* cited by examiner

MEDICAL NAVIGATION SYSTEM USING SHAPE-SENSING DEVICE AND METHOD OF OPERATION THEREOF

CROSS REFERENCE TO RELATED APPLICATIONS

This application is the U.S. National Phase application under 35 U.S.C. § 371 of International Application No. PCT/EP2018/050152 filed Jan. 3, 2018, published as WO 2018/127522 on Jul. 12, 2018, which claims the benefit of U.S. Provisional Patent Application No. 62/441,598 filed Jan. 3, 2017. These applications are hereby incorporated by reference herein.

The present system relates to a navigation system which employs optical shape-sensing fiber (OSS) location methods to determine the position and orientation of a flexible device and, more particularly, to a real-time interventional medical navigation system which employs OSS location methods and detected motion to guide the flexible device through a tissue mass to a determined location, and methods of operation thereof.

In medical procedures (hereinafter procedures for the sake of clarity), real-time information about the spatial position and orientation (i.e., the "pose") of a medical device is often required. The pose of a medical device may be determined using various tracking technologies such as electromagnetic (EM) tracking, OSS tracking methods, Computed tomography (CT) scans, X-ray tracking, fluoroscopy tracking and the like. Unfortunately, real-time tracking of medical devices in vivo during an interventional procedure such as a biopsy may be difficult, if not impossible, for many reasons. For example, performing a biopsy upon a peripheral lung lesion via an endobronchial approach is extremely challenging for many reasons such as: 1) conventional bronchoscopes are too large to fit down the small airways, therefore, visualization is lost and tools must be navigated blindly outside of the airways, 2) complex structures of the airways may limit the usefulness of fluoroscopy, and 3) respiratory and cardiac motion may cause medical devices such as tools and implements to move significantly during interventional procedures. For these reasons and others it may be difficult, if not impossible, for a surgeon to guide a medical device to a desired location, such as a tumor, during a surgical intervention in vivo using conventional devices and methods.

Although tracking technologies, like EM navigation, have been proposed to help address the problem of navigating blindly in the peripheral airways, these tracking techniques only rely on a locating device being at the tip of the tool. Unfortunately, respiratory and cardiac motion cause large deformations in the lung thus decreasing the accuracy of single-point-based tracking technologies. Further, with regards to X-ray and CT tracking systems, these systems are expensive and may subject a patient and those about the patient such as clinicians to high doses of radiation especially when used during interventional type procedures.

Accordingly, embodiments of the present system may overcome these and other disadvantages of conventional tracking-systems and methods.

The system(s), device(s), method(s), arrangements(s), user interface(s), computer program(s), processes, etc. (hereinafter each of which will be referred to as system, unless the context indicates otherwise), described herein address problems in prior art systems.

In accordance with embodiments of the present system, there is disclosed a medical navigation system which may include: a shape-sensing device (SSD) which senses position and orientation along its length and generates corresponding SSD information (SSDI); and a controller which may be configured to: generate a three-dimensional (3D) volume based upon image information of a region of interest (ROI) generated by an imager, determine a reference path (RP) to an object-of-interest (OOI) situated within the ROI, the RP defining an on-road path (ONP) through at least one natural pathway of an organ subject to cyclical motion and an adjacent off-road path (ORP) through tissue of the organ leading to the OOI, and an exit point situated between the ONP and the ORP, query the SSD to obtain SSDI when the SSD is situated within the at least one natural pathway and is subject to the cyclical motion, determine a shape and a pose of the SSD based upon the SSDI obtained when the SSD is situated within the at least one natural pathway and is subject to the cyclical motion, calculate an error between the RP and the determined shape and pose of the SSD, and/or determine when or where to exit a wall of the natural pathway and begin the ORP based upon the calculated error.

It is envisioned that the controller may be further configured to render a graphical user interface (GUI) with the RP and shape of the SSD superimposed upon the 3D volume and an indication of the calculated error. The controller may also be configured to determine when the calculated error is at a minimum value in real time. Further, when it is determined that the calculated error is at a minimum value, the controller may be configured to render an indication to begin the ORP.

It is also envisioned that the controller may determine when a distal tip of the SSD is substantially located at the end of the ONP. The controller may be further configured to query the SSD to acquire SSDI and determine a pose of the distal tip of the SSD, when it is determined that a distal tip of the SSD is substantially located at the end the ONP. The controller may be further configured to determine an expected trajectory of a distal tip of the SSD through the ORP based upon the pose of the distal tip of the SSD determined in accordance with SSDI acquired when the distal tip of the SSD is determined to be substantially located at the end the ONP. The controller may be further configured to determine an angular error between an expected trajectory of the distal tip of the SSD and the RP for the ORP and render the determined angular error when a distal tip of the SSD is determined to be substantially located at the end the ONP. It is further envisioned that the system may include at least one robotic controller that may be configured to control motion of the SSD in accordance with navigation information generated by the controller.

In accordance with embodiments of the present system, there is disclosed a medical navigation method, the method being performed by a controller and may include acts of: sensing, by an SSD, position and orientation along a length of a shape-sensing device (SSD) and generating corresponding SSD information (SSDI); generating a three-dimensional (3D) volume based upon image information of a region of interest (ROI) acquired by an imager; determining a reference path (RP) to an object-of-interest (OOI) situated within the ROI, the RP defining an on-road path (ONP) through at least one natural pathway of an organ subject to cyclical motion and an adjacent off-road path (ORP) through tissue of the organ leading to the OOI, and an exit point situated between the ONP and the ORP; querying the SSD to obtain SSDI when the SSD is situated within the at least one natural pathway and is subject to the cyclical motion; determining a shape and a pose of the SSD based upon the SSDI obtained when the SSD is situated within the at least one natural pathway and is subject to the cyclical motion;

calculating an error between the RP and the determined shape and pose of the SSD; and/or determining when or where to exit a wall of the natural pathway and begin the ORP based upon the calculated error.

It is further envisioned that the method may include an act of rendering a GUI with the RP and shape of the SSD superimposed upon the 3D volume and an indication of the calculated error. Moreover, the method may include an act of determining when the calculated error is at a minimum value. It is also envisioned that the method may include an act of rendering an indication to begin an ORP when it is determined that the calculated error is at a minimum value. The method may further include an act of querying the SSD to acquire SSDI and determining a pose of the distal tip of the SSD, when a distal tip of the SSD is determined to be substantially located at the end the ONP. The method may also include an act of determining an expected trajectory of a distal tip of the SSD through the ORP based upon the determined pose of the distal tip of the SSD. Further, the method may include an act of determining an angular error between an expected trajectory of the distal tip of the SSD and the RP for the ORP, and/or rendering the determined angular error when a distal tip of the SSD is determined to be substantially located at the end the ONP.

In accordance with yet further embodiments of the present system, there is disclosed a non-transitory computer readable medium comprising computer instructions which, when executed by a processor, configure the processor to perform acts of: sensing, by an SSD, position and orientation along a length of a shape-sensing device (SSD) and generating corresponding SSD information (SSDI); generating a three-dimensional (3D) volume based upon image information of a region of interest (ROI) acquired by an imager; determining a reference path (RP) to an object-of-interest (OOI) situated within the ROI, the RP defining an on-road path (ONP) through at least one natural pathway of an organ subject to cyclical motion and an adjacent off-road path (ORP) through tissue of the organ leading to the OOI, and an exit point situated between the ONP and the ORP; querying the SSD to obtain SSDI when the SSD is situated within the at least one natural pathway and is subject to the cyclical motion; determining a shape and a pose of the SSD based upon the SSDI obtained when the SSD is situated within the at least one natural pathway and is subject to the cyclical motion; calculating an error between the RP and the determined shape and pose of the SSD; and/or determining when or where to exit a wall of the natural pathway and begin the ORP based upon the calculated error.

It is further envisioned that the system may be further configured to perform an act of rendering a GUI with the RP and shape of the SSD superimposed upon the 3D volume and an indication of the calculated error. It is also envisioned that the processor may be further configured to perform an act of determining when the calculated error is at a minimum value in real time. The processor may also be configured to perform an act of rendering an indication to begin an ORP when it is determined that the calculated error is at a minimum value. The processor may further be configured to perform an act of querying the SSD to acquire SSDI and determining a pose of the distal tip of the SSD, when a distal tip of the SSD is determined to be substantially located at the end the ONP.

The present invention is explained in further detail in the following exemplary embodiments and with reference to the figures, where identical or similar elements are partly indicated by the same or similar reference numerals, and the features of various exemplary embodiments being combinable. In the drawings.

Figure 1:
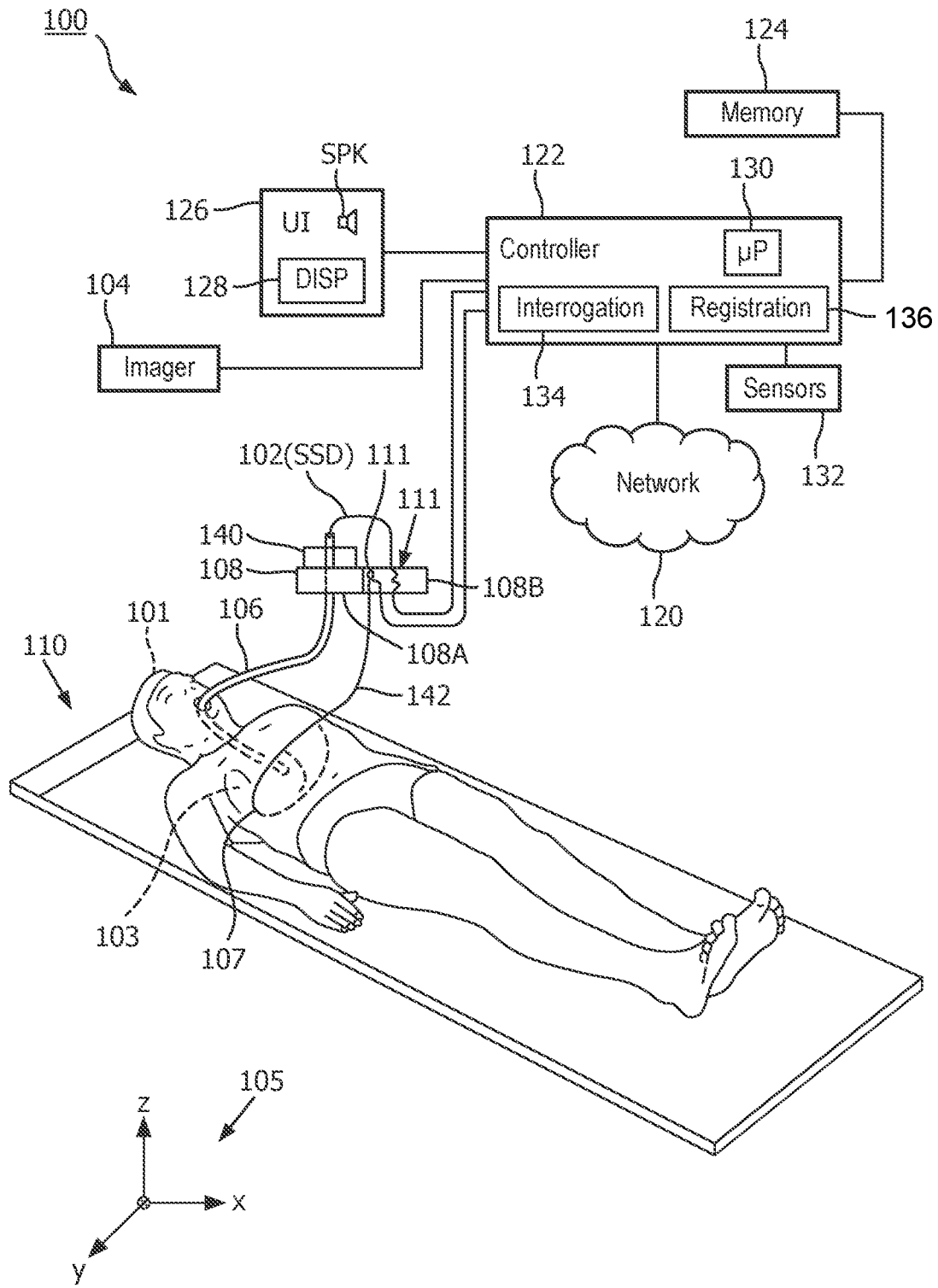
FIG. 1 shows a perspective front view of a portion of a navigation system operating in accordance with embodiments of the present system.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements. The term and/or and formatives thereof should be understood to mean that only one or more of the recited elements may need to be suitably present (e.g., only one recited element is present, two of the recited elements may be present, etc., up to all of the recited elements may be present) in a system in accordance with the claims recitation and in accordance with one or more embodiments of the present system.

Embodiments of the present system may provide real-time information about spatial position and orientation (i.e., the "pose") of a medical device during use such as during an interventional procedure. For the sake of clarity, exemplary embodiments of the present system may be illustratively described with reference to a shape-sensing device (SSD) inserted within a channel of an endoscope or endoscope-like device. The SSD may then be considered to be embedded within the endoscope. However, it should be understood that SSDs in accordance with embodiments of the present system may otherwise be associated with the medical device such that from position information of the SSD, the position of the medical device may be determined in real-time. In accordance with embodiments of the present system, the SSD may be operative with and/or combined with various devices such as medical instruments, which, without limitation, may include, one or more of catheters, endoscopes, bronchoscopes, laparoscopes, guide wires, sheaths, a probe such as an ultrasound probe, biopsy tools including one or more of a brush, forceps, other surgical tools and/or other medical devices (e.g., ablators, ultrasound probes, sensors, cameras, grippers, cutters, brushes, needles suctioning tools, biopsy tools, therapy tools, etc.), to provide information related to the three-dimensional shape (3D) and pose (e.g., position and orientation) of the SSD and the combined device. Further, it should be understood that SSDs of the present system may be used alone or with one or more other medical devices. For example, the introducer 106 may include any suitable flexible or rigid device which may be suitable for a procedure being performed. Illustratively, in a case wherein the procedure being performed is a lung biopsy or the like, the introducer 106 may be a bronchoscope or the like. Similarly, in a case wherein the procedure being performed is a vascular procedure, the introducer 106 may be a catheter or a sheath. For other areas or types of procedures, the introducer 106 may be an endoscope or laparoscope or the like. For the sake of clarity, embodiments of the present system will be shown and described with respect to an introducer (such as a bronchoscope), tool and/or other device however should be understood to encompass any such device that may be suitably applied for a given intervention.

For example, a distal end of an SSD may be inserted into an opening or a channel of an introducer or may be attached to the introducer in some other manner. By knowing a position and orientation of this opening relative to the introducer, the pose of the corresponding device may be determined based upon a known shape of the SSD. In other embodiments, the introducer may simply be the SSD either incorporated as a portion of the introducer and/or as the introducer itself (i.e., without other devices present).

With regard to the SSD, suitable tracking methods may be discussed in, for example, U.S. Pat. No. 8,050,523; and U.S. Patent Application No.: 2015/0012011, the contents of each of which are incorporated herein by reference although clearly other SSDs may also be suitably applied in accordance with embodiments of the present system.

For the sake of clarity, embodiments of the present system will be shown and described with respect to shape sensing devices (SSDs) such as shape-sensing fibers (SSFs) as may be employed using Fiber-Optic RealShape™ (FORS) methods and the like. Thus, the SSDs may include FORS-type devices employing FORS methods. However, it is also envisioned that embodiments of the present system may be compatible with other tracking systems which may sample multiple data points sequentially or simultaneously such as EM tracking methods and the like.

The SSD and/or introducer may further include a feedback sensor such as a force/pressure feedback at the distal end thereof to sense pressure on the distal end and provide an indication of this pressure. Accordingly, the system may provide an indication of when the introducer/SSD is in contact with a solid or semi-solid structure such as an airway wall, a lesion, a tumor, etc. This information may be useful to determine, for example, when the introducer/SSD has reached a desired exit point of an airway (e.g., as may be detected by increased force obtained from the feedback sensor) at which point the introducer may puncture through the wall of the airway at the desired exit point to go off-road (e.g., outside of a naturally occurring conduit, such as a breathing airway, blood vessel, bowel, etc.) to reach a desired object-of-interest (OOI) such as a lesion, a tumor, etc., for example that may be positioned outside of the conduit or be positioned within a portion of the conduit that is otherwise inaccessible to the introducer. However, as readily appreciated there may be other reasons (e.g., to navigate around a blockage, a blood vessel, etc.) for going off-road while in route to a desired position.

FIG. 1 shows a perspective front view of a portion of a navigation system 100 (hereinafter system 100 for the sake of clarity) operating in accordance with embodiments of the present system. The system 100 may include one or more of an SSD 102, an imager 104, a launch base 108, a introducer 106, a support platform 110, a controller 122, a robotic controller 140, a network 120, a memory 124, sensors 132, a user interface (UI) 126, and a breathing monitor 142. For clarity, the present system is illustratively described with regard to the introducer 106 as the illustrative medical device however, it should be explicitly understood that one or more other medical devices may be suitably employed alone or together with the introducer 106.

The controller 122 may control the overall operation of the system 100 and may communicate with one or more of the SSD 102, the imager 104, the launch base (hereinafter base) 108, the introducer 106, the support platform 110, the robotic controller 140, the network 120, the memory 124, the sensors 132, the user interface (UI) 126, and the breathing monitor 142 using suitable wired and/or wireless communication methods such as via a wired and/or wireless bus, the network 120, etc.

The imager 104 may include one or more imaging modalities such as a magnetic resonance imaging (MRI) imager, a computed tomography (CT) scanner, an X-ray imager (e.g., an interventional X-ray imager), an ultrasound imager, cameras, a fluoroscopy imager, and/or combinations thereof. The imager 104 may provide image information to the controller 122 in any suitable format (e.g., raw, processed, digital, etc.) for further processing such as for analysis of data, reconstruction, storage, etc. In accordance with embodiments of the present system, the imager 104 may obtain pre-operative CT scans (e.g., fluoroscopy images) and together with the controller 122 may form a corresponding pre-operative 3D volume.

The robotic controller 140 may be operative to robotically manipulate one or more surgical devices of the present system such as the introducer 106 to a desired shape, position and/or orientation under the control of the controller 122. Accordingly, for example, the robotic controller 140 may receive navigation information generated by the controller 122 and robotically manipulate one or more introducers of the present system such as the introducer 106 to a desired shape, position and/or orientation accordingly. Similarly, the robotic controller 140 may control one or more devices associated with the introducer 106. Accordingly, the robotic controller 140 may include one or more actuators, arms, etc. to manipulate the introducer 106 and/or other medical device(s) for example associated with the introducer 106 as a unit or independently of each other as may be desired. Further, robotic controller 140 may include a mechanical or electro-mechanical manipulation portion with which a user may manipulate or enter commands to manipulate the introducer 106/medical device(s) and/or portions thereof. For example, the UI 126 may include a user input device such as joystick or the like with which a user (e.g., a surgeon) may enter commands (e.g., which may be generated as a signal and/or force) to control the pose of one or more portions of the introducer 106/medical device(s). Accordingly, a distal end 107 of the introducer 106 may be manipulated to a desired area within a patient 101 such as within a lung 103 of the patient 101. The robotic controller 140 may be coupled to the base 108 as may be desired. It is envisioned that manual and/or automatic control may be provided such that the introducer 106 and/or the devices, etc. may be automatically and/or manually controlled by a user. Thus, manual and/or robotic manipulation of the introducer 106, the SSD 102, and/or device(s) may be provided.

The breathing monitor 142 may include any suitable breathing monitor to determine a respiratory cycle of the patient. For example, the breathing monitor 142 may include an SSD-type breathing monitor which may supply information to determine a respiratory cycle. The breathing monitor 142 may monitor breathing of the patient 101 and form corresponding breathing information which may be provided to the controller 122 for further processing such as for determining a point in the respiratory cycle (e.g., breathing phase) of the patient 101 in real time. As may be readily appreciated, the breathing monitor 142 may form a portion of the SSD 102 and/or may be separate from it as desired. In an embodiment wherein the breathing monitor 142 is separate from the SSD 102, real time information on a where the patient is in the breathing cycle may be provided even when the SSD 102 is otherwise not available such as when the SSD is being inserted, removed, etc.

The network 120 may include any suitable communication link such as a wide-area network (WAN), a local-area network (LAN), the Internet, a system bus, a proprietary bus, the Internet, an intranet, a wired bus, a wireless bus, an ad-hoc network, etc. Accordingly, portions of the system may communicate with other portions of the system via the network 120. It is also envisioned that a user may communicate with the system using local and/or remote communication methods via the network 120.

The memory 124 may include any suitable non-volatile memory in which information such as operating instructions, information generated by the system, user inputs and/or settings, historical information, operating settings and/or parameters, identification information, user information, patient information, etc., may be stored.

The sensors 132 may include sensors which may obtain corresponding sensor information and provide this sensor information to the controller 122 for further processing. For example, the sensors 132 may include optical-shape-sensors such as FORS-type sensors, which may sense a shape of the SSD 102 and/or provide corresponding information (e.g., SSD information (SSDI)) to the controller 122 which may determine shape, position and/or orientation of one or more portions of the SSD 102 in accordance with embodiments of the present system and may form corresponding shape, position and/or orientation information. The sensors 132 may be distributed throughout the system 100 and may further include sensors such as touch sensors, pressure sensors, force-sensors, ambient condition sensors, etc. The sensors 132 may further include user input devices (e.g., a keyboard, a touch-screen, a joystick, etc.), etc., with which a user may enter information into the system. Further, the sensors 132 may include position sensors which may provide position/orientation information related to a position/orientation of the table 110, the patient 101, the base 108, the robotic controller 140, etc.

The UI 126 may include any suitable user interface which may render information for the convenience of the user such as graphical user interfaces (GUIs) generated by the system and/or image information. Accordingly, the UI 126 may include a speaker (SPK), a display 128 (e.g., a touch-screen display, etc.), haptic device (e.g., vibrators, etc.). Further, the UI 126 may include a user interface with which a user may control one or more portions of the system 100 such as the introducer 106, the robotic controller 140, and/or devices which may be inserted alone and/or in conjunction with the introducer 106. For example, the UI 126 may include a joystick controller, etc., with which a user may enter commands to control the introducer 106 and/or other portions of the system 100 such as other devices, etc. In accordance with embodiments of the present system, the one or more devices may be inserted within, and/or guided, at least partially by the introducer 106 to reach an object-of-interest (OOI) such as a lesion, a tumor, suspect tissue, etc. The one or more devices may further be coupled to an SSD so that a shape and/or pose thereof may be determined. For example, the SSD may be queried to obtain SSD information (SSDI) which may be processed by a controller of the system to determine a pose of the corresponding one or more devices.

The support platform 110 may be any suitable support platform which may support an object such as a patient 101 in a desired position and/or orientation for a procedure such as an interventional procedure. The support platform 110 may include actuators which may move the support platform for example under the control of the controller 122.

The base 108 may include any suitable device base or bases (physical or virtual) which may function as a launch fixture for one or more of the introducer 106, the SSD 102 and/or the one or more devices. Further, the base 108 may be configured as a fixation point for a robot or the like such as a robot that may control position, orientation and/or shape of, for example, the introducer 106, the one or more devices, etc. Accordingly, a position and/or orientation at least a portion of one or more of the introducer 106, the one or more devices, and/or the SSD 102 may be determined relative to a reference frame or frames such as the reference frame 105. In accordance with embodiments of the present system, the base 108 may include a plurality of sub-bases which may be coupled together, or to a known portion or portions of the system, such as to locations of the support platform 110. For example, the base 108 may include sub-bases 108A and 108B which may operate as launch fixtures for the introducer 106 and the SSD 102, respectively. Further, the base 108 may be configured to act a base for an actuator of the system which may control shape and/or pose of one or more robotically manipulated portions of the system such as the introducer 106, etc. Although shown coupled together, it is envisioned that these sub-bases may be separated from each other during use or may be integrally formed with each other as may be desired. The base 108 may be coupled to any suitable fixture such as a C arm, the support platform 110, etc.

The base 108 and/or the support platform 110 may include one or more known paths 111 through which the SSD 102 may be placed. When placed through or within these known paths 111, the SSD may assume a shape of the corresponding known paths 111 and form corresponding SSDI. The controller 122 may recognize the corresponding known path (e.g., through an analysis of the SSDI) and determine a position and/or orientation of one or more portions of the SSD 102 relative to the correspondingly recognized known path. Shapes of the known paths 111 may be stored as known path information in a memory of the system for later use such during a registration procedure. The known paths 111 may be registered to corresponding bases 108.

The reference frame 105 may include any suitable reference frames such as a reference frame of the support platform 110, a reference frame of the base 108 (or portions thereof), a reference frame of the patient 101, a common reference frame, etc. For the sake of clarity, it will be assumed that the reference frame 105 may refer to a common reference frame. The system may perform registration to register one or more reference frames to each other and/or a desired one of these reference frames as may be desired.

In accordance with embodiments of the present system, the introducer 106 may be inserted within a desired object such as a body of the patient 101. The introducer 106 may include one or more openings or channels suitable for receiving the SSD 102 so that a position and/or orientation of, for example, a portion of the introducer 106 may be easily determined through an analysis of a pose of the SSD 102. Similarly, the one or more devices may include one or more openings or channels suitable for receiving the SSD 102 so that a position and/or orientation of, for example, a portion of the corresponding device or portions thereof (e.g., a distal end) may be easily determined through an analysis of a pose of the SSD 102. A position of these channels or portions thereof may be known relative to a body of the corresponding introducer 106 and/or device(s). The controller 122 may then render a virtual image of position and/or orientation of the corresponding introducer 106 and/or device(s). For the sake of clarity, it will be assumed that the device may be a bronchoscope. However, it should be understood that in other embodiments the introducer 106 may be replaced with any suitable device which may be guided to a desired location.

The introducer 106 may include one or more openings along a length thereof within which one or more devices and/or SSDs may be inserted to reach a desired location such as an OOI within the patient. In accordance with embodiments of the present system, one or more devices may be inserted serially or simultaneously, within the introducer 106. Further, it is envisioned that the introducer 106 and the SSD 102 may be inserted within the patient through the same or different openings, conduits, conduit portions, etc.

The device(s), the SSD 102, and/or the introducer 106 may communicate with the controller 122 using any suitable wired and/or wireless communication method. For example, the device(s), the SSD 102, and/or the introducer 106 may communicate with the controller 122 via the network 120.

The SSD 102 may include at least one sensor which may provide SSD information suitable for determining a position and/or orientation (e.g., pose) of at least a portion of the SSD 102 relative to a desired reference frame such as the reference frame 105. For the sake of clarity, illustratively the SSD 102 may pass through at least a portion of the opening of the introducer 106 such that a distal end 103 of the SSD 102 may be situated at, or within, one or more of the devices. For example, the SSD 102 may be coupled to the device. However, in yet other embodiments, the SSD 102 may be situated a known distance from the one or more devices, if desired, and a known offset distance and/or orientation may be used to determine the position and/or orientation of the one or more devices. The SSD 102 may further pass through or within a known path such as paths 111 (which may be coupled at a known position and/or orientation to, for example, the base 108) which may be recognized by the system 100 for registration. The introducer 106 may also include a known path so that its pose relative to an SSD may be determined.

Referring back to the controller 122, the controller 122 may control the overall operation of the system 100 and may include one or more logic devices such as processors 130 (e.g., microprocessors (μP), etc.) having multiple interconnected semiconductor devices such as transistors, gates, impedance devices, metallization connections and the like, discrete and/or distributed logic gates and switching devices, and/or the like. The controller 122 may include an interrogation module 134 and/or a registration module 136 which may include hardware, software and/or firmware devices with instructions stored in a memory thereof and/or the memory 124, which when executed by the processor cause the processor (e.g., program the processor) to perform one or more desired functions. The processor so configured becomes a special purpose machine particularly suited for performing in accordance with embodiments of the present system.

The interrogation module 134 may be operative to obtain information from the SSD 102 (e.g., via an interrogation process) such as SSD information (SSDI) (e.g., as described below) and which may indicate a path travelled by the SSD 102 over time and/or a shape of one or more portions of the SSD 102. This path may correspond with a shape of the corresponding SSD and may be determined serially (e.g., over time) and/or simultaneously (e.g., at a single time). The SSDI may be processed to determine the position and/or orientation (e.g., pose) of one or more portions of the SSD 102 such as the pose at its distal portion (e.g., tip). By knowing the shape of the SSD 102, the shape of any devices such as one through which it travels (e.g., introducer 106) may be determined. Similarly, the pose of one or more devices coupled to, or otherwise associated with, the SSD 102 may also be determined. For example, the SSDI of an SSD may be analyzed to determine the pose of the device situated at a tip of the SSD.

The registration module 136 may be operative to perform registration such that one or more devices of the present system may be registered to a desired reference frame such as the common reference frame 105. The registration module 136 may register one or more portions of the system (and/or information obtained therefrom) such as the base 108 (or portions thereof), the known shapes 111, the support platform 110, the imager 104, the SSD 102, the introducer 106, one or more devices associated with (e.g., coupled to) to the SSD, etc., to a desired reference frame such as the reference frame 105. For example, it is envisioned that the registration module 136 may register images obtained from one or more imaging modalities of the imager 104 to each other, the SSD, and/or the reference frame 105 and/or to the known shapes 111.

The SSD 102 may be formed using any suitable shape-sensing device such as a Fiber Optic RealShape™ (FORS) fiber or the like which may provide SSD sensor information (e.g., SSDI) from a plurality of sensors indicative of position and/or orientation of a plurality of locations along its length. For example, the SSDI may provide information related to, for example, a position (e.g., an x, y, z coordinate, etc.) and/or orientation (e.g., twist of a corresponding fiber) of each corresponding shape sensing sensor at a shape sensing sensor location. The plurality of shape sensing locations may approach a continuum of locations, if desired. However, generally, the plurality of shape sensing locations may be set apart from each other by a desired distance such as 40 μm or other suitable distance. Thus, the shape sensing locations may be spread throughout the SSD 102. Suitable SSDs 102 may include, for example, a shape sensing fiber (SSF), an EM-based tracking device with at least one EM sensor such as an EM sensor located at a tip thereof, etc. The SSF may include any suitable shape-sensing multicore optical fiber which may employ Rayleigh (enhanced or regular), Fiber Bragg, etc. detection methods.

With regard to the SSFs, these fibers may include sensors such as active light emitting diodes (LEDs), passive reflectors such as spheres, optical and/or EM coils, and/or radioactive or radiopaque markers which are identifiable based on imaging such as X-ray and/or nuclear based imaging. Similarly to the optical sensors, the EM sensors and/or other sensors/markers may be situated at one or more locations apart from each other as may be desired, or a shape may be reconstructed from a single point sensor by accumulating a history of positions as the SSD 102 is passed through a path.

During operation, the SSDI may be obtained by interrogating the SSD 102 using any suitable method. The interrogation techniques utilized may correspond with a type of the SSD 102 employed by the system. For example, the SSF may employ the FORS technology to determine position and/or orientation thereof to obtain the SSDI. However, it should be understood that these interrogation techniques may or may not be exclusive of each other. Further, the optical interrogation technique may interrogate at least one optical sensor of the SSD 102 synchronously in time. In accordance with embodiments of the present system, the FORS technology may be replaced or supplemented with an electromagnetic (EM) tracking system including an EM sensor in the SSD to obtain the SSDI.

Regardless of the type of interrogation technique, the interrogation may obtain the SSDI which may then be processed to perform a registration of the SSD 102 to a desired reference frame such as reference frame 105 and to determine a shape of the SSD 102.

The controller 122 may be communicatively coupled (using any suitable method such as electronically, optically, etc.) to the SSD 102 so that the SSD 102 may be interrogated. For the sake of clarity, it will be assumed that the workspace of the patient 101 may be referred to as a reference workspace. However, it should be understood that there may be several reference workspaces in a system operating in accordance with embodiments of the present system.

Referring back to the SSD 102, optical shape sensing (OSS) embodiments of the present system may distribute light along a multicore optical fiber such as optical-shape sensing fibers (OSSFs) for obtaining SSDI. The SSDI may then be analyzed to determine shape of the SSD, pose of portions of the SSD such as a distal end (e.g., a tip) of the SSD. The SSDI may further be analyzed and the results used for registration, device localization and navigation during use such as during a surgical intervention. In accordance with embodiments of the present system, distributed strain measurements in the optical fibers (of the SSF) may be performed using characteristic Rayleigh backscatter or controlled grating-patterns. The shape along the SSD 102 may begin at a specific point along the SSD 102, known as the launch or z=0, and the subsequent shape of the SSD 102 may be defined relative to that point (e.g., the launch point) through a distal end point of the SSD 102. Similarly, the pose of one or more portions of the SSD 102 such as the distal end of the SSD may be determined.

In accordance with embodiments of the present system, the SSD 102 may be integrated with one or more guide wiredevices to provide live guidance of the corresponding devices during minimally invasive procedures. Further, the SSD 102 may be integrated with the introducer 106.

By knowing the shape and/or pose of the SSD, the shape and/or pose of the associated device(s), such as the introducer or portions thereof, may be determined. Thus, the position and/or orientation of the associated device and/or portions thereof, may be determined in real-time in accordance with embodiments of the present system.

When one more SSDs may be incorporated into a bronchoscope or catheter, the combination may be referred to as a universal-catheter (e.g., a uni-cath). Similarly, when one more SSDs 102 may be incorporated into a bronchoscope, the combination may be referred to as a universal-bronchoscope (UB). A universal catheter hub may be used in conjunction with the SSD 102 to virtually sense devices which are associated with (e.g., runs over, along, is coupled to, etc.) the corresponding SSD 102 such as a catheter, a bronchoscope, a guide wire, a biopsy tool, etc. When the SSD 102 is embedded with a guide wire, the combination may be referred to as a shape-sensed guide wire (SSG) and when the SSD is embedded with a biopsy tool, the combination may be referred to as a shape-sensed-biopsy-tool (SSBT). By embedding the SSD with a device, the SSDI may be used to determine the shape as well as pose of one or more portions of the combined device. The SSG and SSBT may be generally referred to as a SSD tool unless the context indicates otherwise.

By using a separate breathing monitor 142, this operation need not be performed by the SSD and information from the separate breathing monitor 142 may be used to determine and/or confirm (i.e., wherein the SSD also provides information on the respiratory cycle) a point in the respiratory cycle of the patient. By monitoring the respiratory cycle of the patient, respiratory motion is monitored and is used for navigation.

Figure 2:
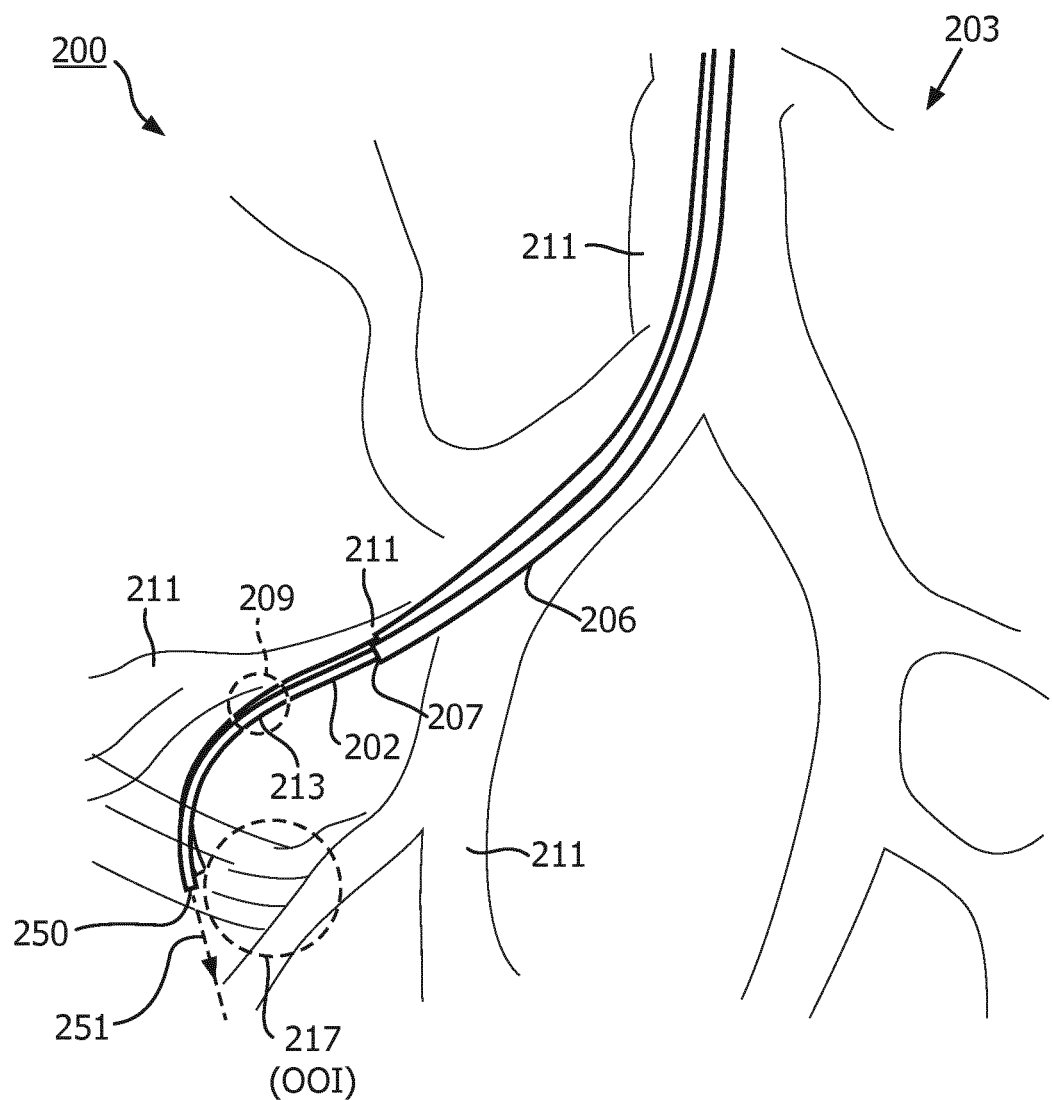
FIG. 2 shows a virtual image of an SSD tool and a bronchoscope superimposed upon a 2D image obtained from an x-ray (or the like) of a lung of a patient rendered in accordance with embodiments of the present system.

FIG. 2 shows a virtual image 200 of an SSD tool 202 (e.g., a SSG) and a bronchoscope 206 superimposed upon a 2D image illustratively obtained using a universal catheter hub from fluoroscopic imaging of a lung 203 of a patient rendered in accordance with embodiments of the present system. In the illustrative embodiment, these virtual tools are overlaid on a 2D fluoroscopy image of a lung including a bronchoscope and further device. In further embodiments, a 3D reconstructed volume of the airways may be provided with the virtual SSD tool and other devices superimposed.

The SSD tool 202 may extend through a channel of a suitable guidance device such as the bronchoscope 206 to a desired position within the lung 203 of the patient. The system may register the SSD tool 202 and by association the bronchoscope 206 to a common reference frame using any suitable method. The system may obtain SSDI from the SSD tool 202 and determine a shape as well as a pose of the SSD tool 202 in accordance with the SSDI. Then, knowing the shape of the SSD tool 202, the shape and pose of the bronchoscope 206 may be determined.

The system may generate and superimpose a virtual image of the SSD tool 202 and the bronchoscope 206 upon a 2D/3D image volume obtained from the imaging device such as a fluoroscopy image as shown. Although the present embodiments illustrate a 2D/3D image volume formed using an fluoroscopy imaging method, other types of imaging methods (e.g., MRI, CT, X-ray, ultrasound, etc.) may also be employed with (e.g., using layering of registered images), or in lieu of, the fluoroscopy images. Accordingly, the 2D/3D image volume may include a plurality of superimposed images obtained from different types of imaging methods. Further, it is envisioned that the images may be acquired, reconstructed, and/or rendered in real time or may be delayed, as may be desired.

The bronchoscope 206 may be situated within one or more airways 211 of the lung 203 of the patient. A distal portion of the SSD tool 202 may extend from the bronchoscope 206 through the corresponding airway 211 and may thereafter exit through a wall of the corresponding airway 211 at point 213 of area 209 so that a distal end 250 (e.g., a distal tip) of the SSD tool 202 may be situated at a desired object-of-interest (OOI) 217 which, may be any suitable biological mass (e.g., a lesion, a tumor, etc.). The system may employ real-time mapping methods to determine airways 211 to navigate within and when to exit the corresponding airway 211 and go "off-road" (hereinafter off-road or off-roading). When going off-roading, the shape and pose of the SSD tool 202 may be used to determine the pose of a distal end 250 of the SSD tool 202. By knowing this pose, a travel vector 251 may be determined. The travel vector 251 may be linear or non-linear and may be dynamically determined. This travel vector 250 may be used to determine a path in which the SSD tool 202 may travel when advanced (e.g., through a tissue mass of the lung 203) when off-roading.

In accordance with embodiments of the present system, an interventional X-ray imager may be employed to more precisely update a registration between the pre-operative image (e.g., one or more pre-op CT scans) and a determined shape of the SSD (e.g., as indicated by SSDI). For instance, low-frame-rate fluoroscopy image may be acquired during an entire phase where shape of the SSD is recording during a full respiratory cycle. In accordance with embodiments of the present system, though not required, this may improve registration of the determined shape of the SSD for more precise guidance. The X-ray information may also be used to morph a pre-operative CT scan to display natural pathways (e.g., airways of a lung), a reference path, and/or anatomy during other points of the respiratory cycle.

Figure 3:
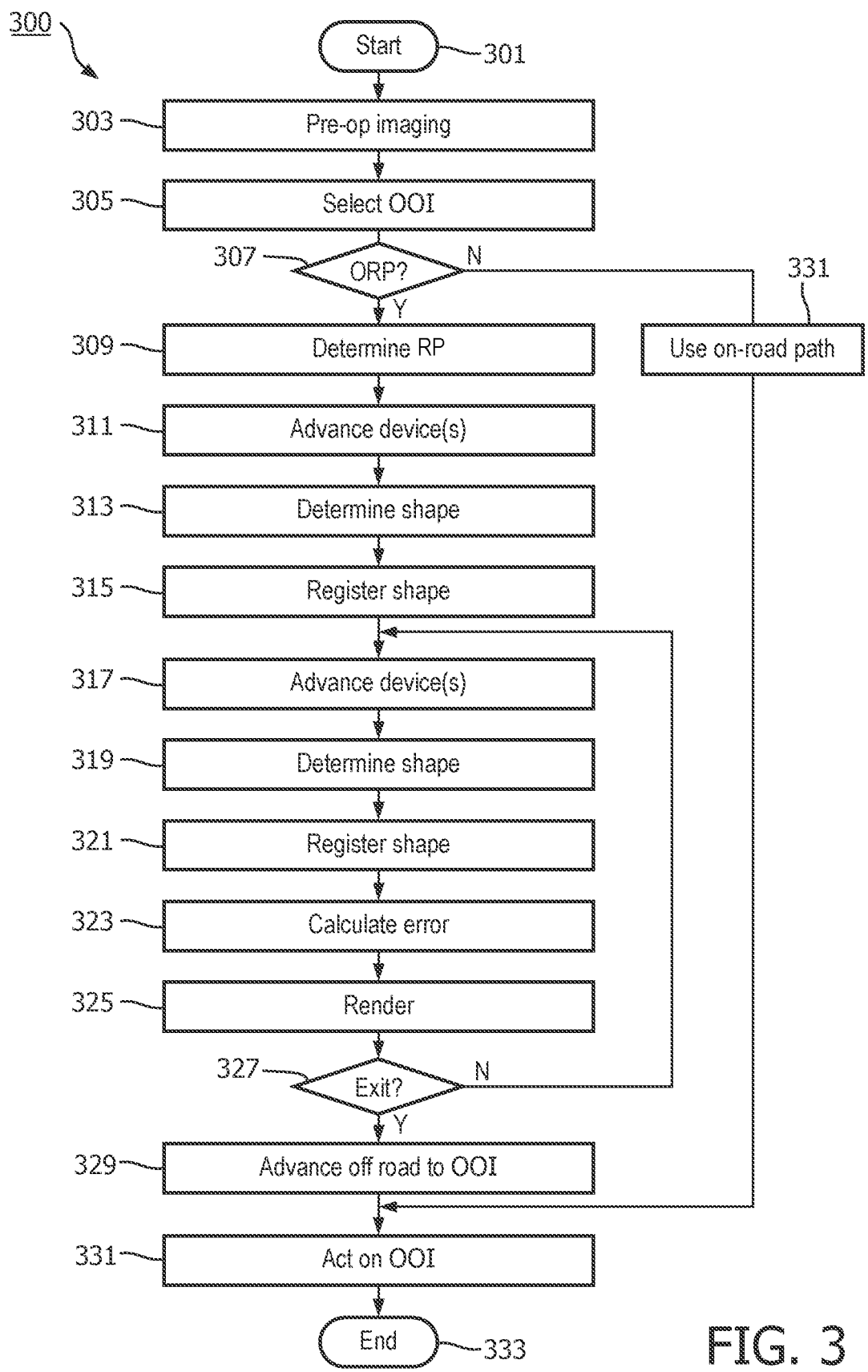
FIG. 3 shows a functional flow diagram performed by a process in accordance with embodiments of the present system.

A process to navigate within an organ such as a lung to an OOI such as a lesion, a tumor, or the like within the corresponding organ in accordance with embodiments of the present system is illustratively described with respect FIG. 3.

FIG. 3 shows a functional flow diagram performed by a process 300 in accordance with embodiments of the present system. The process 300 may be performed using one or more processors, computers, controllers, etc., communicating over a network and may obtain information from, and/or store information to one or more memories which may be local and/or remote from each other. The process 300 may include one of more of the following acts. In accordance with embodiments of the present system, the acts of process 300 may be performed using one or more suitable coordinate registration systems operating in accordance with embodiments of the present system. Further, one or more of these acts may be combined and/or separated into sub-acts, as desired. Further, one or more of these acts may be skipped depending upon settings. For the sake of clarity, the process may be described with reference to a bronchoscope and SSD tool (e.g., a biopsy device in the present embodiments) the latter of which may pass through a channel of the bronchoscope. However, without limitation, it should be understood that the process may employ a plurality of devices and/or SSD tools each of which may include a separate, or partially separate, workflow. In operation, the process may start during act 301 and then proceed to act 303. Although the process 300 will be described with reference to a single lesion, portions of it may be repeated for a plurality of lesions or other ROIs.

During act 303, the process may perform pre-operative imaging to acquire image information using one or more selected imaging modalities of the system such as fluoroscopy imaging of a region of interest (ROI). The acquired image information may be reconstructed to form a corresponding pre-operative 2D and/or 3D volume which may be generally referred to for example as a 2D and/or 3D volume. The ROI may include an object-of-interest (OOI) which may be assumed to be a lesion in the present examples for the sake of clarity.

In the present embodiments, it is assumed that a 3D volume (and/or other 3D volumes) may be formed of reconstructed images acquired using fluoroscopy imaging methods for the sake of clarity. However, without limitation it should be understood that other imaging methods may be employed by the system with, or in lieu of, the fluoroscopy method of the present embodiments.

The process may render the 3D volume (or portions thereof) on a rendering device of the system for the convenience of the user. It is also envisioned that the process may provide a user interface (UI) such as a graphical user interface (GUI) with which a user may interact with the system to, for example, select lesions, natural pathways such as airways of the lung in the present embodiments, etc., within the 3D volume. Accordingly, the process may determine features within the 3D volume such as landmarks (e.g., airways, airway walls, lesions, tumors, masses, etc.). These landmarks may be selected based upon a type of procedure being performed. For example, when performing a lung biopsy as in the present illustrative embodiments, the system may detect a desired lesion and natural pathways such as (breathing) airways and their walls (e.g., airway walls). Accordingly, in the present embodiments, the natural pathway will reference (breathing airways of the lung) and the channel walls will reference the walls of these breathing airways unless the context indicates otherwise.

Thus, embodiments of the present system may be suitable for operation with other types of procedures with minimal modifications such as by substitution. For example, embodiments of the present system may be suitable for vascular tract procedures by substituting the vascular tract and the vascular tract walls for the natural pathway and the walls of the natural pathway, respectively. A similar substitution may be made with intestinal tract procedures by substituting the intestinal tract and the intestinal tract walls for the natural pathway and the walls of the natural pathway, respectively. Lastly, a similar substitution may be made for cardiac procedures by substituting the cardiac chambers and the cardiac walls for the natural pathway and the walls of the natural pathway, respectively.

Regardless of the type of procedure being performed, the system may determine corresponding natural pathways (NPs) and OOIs such as lesions automatically or in accordance with user input. As the present procedure is illustratively described as a lung biopsy, the ROI may be assumed to include the lung of a human patient for the sake of clarity. However, without limitation, it is envisioned that the ROI may also include other portions of an anatomy of humans and other animals such as those of the cardiac, vascular or gastrointestinal tracts, etc. depending upon a type of procedure being performed. After completing act 303, the process may continue to act 305.

During act 305, the process may select an OOI from within the ROI as represented by the 3D volume. For example, the OOI may be assumed to be a lesion within a lung of a patient in the present embodiments. However, other types of OOIs are also envisioned. The OOI may be selected by the system automatically (e.g., using image analysis methods or the like to detect tumors, desired portions, etc.) or may be selected by a user from within the 3D volume which may be rendered on a rendering device of the system. For example, the system may render a GUI including the 3D volume and the user may interact with the GUI to select one or more OOIs such as lesions, etc., to which navigation to by the SSD tool as desired. The GUI may further provide selection items for a user to interact with to manipulate views of the 3D volume and/or select and/or tag features of the 3D volume using 2D or 3D methods. After completing act 305, the process may continue to act 307.

During act 307, the process may determine whether it may be necessary to use an off-road path (ORP) (e.g., to off-road) to reach the selected OOI. Accordingly, in a case wherein it is determined that an ORP may be necessary to use to reach the selected OOI, the process may continue to act 309. However, in a case wherein it is determined that an ORP may not be necessary to use to reach to the selected OOI, the process may continue to act 331. The process may determine that it may be necessary to use an ORP to reach to the selected OOI, when it is determined that the selected OOI is not connected to a natural pathway or lies in a periphery of a natural pathway having a diameter (or cross section) of corresponding natural pathway that is less than a threshold diameter (e.g., 0.5 mm in diameter the current examples). This threshold diameter may be related to the diameter of the corresponding SSD tool. Thus, when the diameter of the corresponding natural pathway is less than the threshold diameter, the SSD tool cannot advance through this natural pathway without using an ORP. However, when the diameter of the corresponding natural pathway is greater than or equal to the threshold diameter, the SSD tool may travel through the natural pathway without using an ORP. This determination may be made using any suitable analysis (e.g., image analysis) techniques of the acquired 3D image volume. Thus, OOIs which are determined not to be adjacent to a natural pathway such as an airway accessible by an SSD tool may be determined to require an ORP to reach.

It is also envisioned that the user may select whether the ORP is desired or to override use to reach the selected OOI. For example, selection items on the GUI may be provided for the user to make this selection. Further, the system may render information of whether it may be necessary to use an ORP to navigate to the selected OOI for the convenience of the user. For example, the system may render information such as (e.g., "selected lesion requires off-road access method" or "selected lesion does not require off-road access method").

During act 309, the system (e.g., one or more processors) may perform 3D volume and path planning to determine a reference path (RP) for guiding one or more selected surgical implements, such as the bronchoscope (e.g., a UB) and an SSD tool such as a SSGT or a SSBT in the present embodiments, to the OOI using an ORP. The RP may define sub-portions such as a natural pathway portion and an ORP wherein the natural pathway portion corresponds with the natural pathway (e.g., the airway in the present embodiments). For the sake of clarity, the surgical device may refer to the bronchoscope and/or the SSD tool in the present embodiments. However, it is envisioned that other surgical implements may also be similarly employed depending upon a procedure being performed. For example, depending upon a type of procedure being performed, a catheter may be substituted for the bronchoscope. Similarly, different types of tools such as an ablator, a biopsy tool, an ultrasound probe, a gripper, etc. may be substituted for the SSD tool as may be desired. Moreover, the SSD tools may be withdrawn and replaced during an intervention. For example, an SSBT may be substituted for an SSG during an intervention.

The RP may be determined such that it may travel within one or more natural pathways (e.g., airways of the lungs) of the patient and thereafter exit through a wall of the natural pathway and proceed off road through tissue (e.g., lung tissue) to the OOI. For example, the RP may define a path which travels via at least one natural pathway (such as the airways of the lung of the patient) to an exit point (e.g., in the wall of the lungs) at which time this path may proceed off road to the selected OOI. The RP may be considered a virtual trajectory and may be an optimal or substantially optimal path to travel to the OOI through the corresponding natural pathway. Path planning may be performed using any suitable path planning methods, algorithms, application(s) and/or the like such as EmboGuide™, Super Dimension™, and the like.

It is envisioned that at least a portion of the RP may be determined by a user. For example, the user may interact with the system to select at least a portion of the RP such as an entry point at which the surgical implements may enter the lung and/or one or more desired natural pathways (e.g., airways) through which the surgical device (e.g., bronchoscope, etc.) and/or SSD tool may travel to reach the OOI. Thus, knowing a desired portion of the RP (e.g., the entry point), the system may plan the rest of the RP, if desired. Further, the system may determine a plurality of paths for selection by a user who may select one of these paths as the RP. For example, the system may render a plurality of proposed paths upon a rendering of the 3D volume and the user may select one of these paths as a RP. Further, once the RP is determined, the process may render the RP superimposed upon the pre-operative 3D volume for the convenience of the user. When determining the RP, the system may take into account cyclical motion within the ROI such as cardiac motion and motion due to breathing of the patient. This motion may be determined for at least one cycle, as desired.

In accordance with embodiments of the present system, the entry point may be detected automatically by the system such as by using an imaging apparatus or SSDI which may define an entry point as may be desired. After completing act 309, the process may continue to act 311.

During act 311, one or more of the surgical devices, such as one or more of the bronchoscope and/or SSD tool, may be advanced a threshold advance distance (TAD) within the natural pathway defined by, or substantially by, the RP. This advancement may be performed automatically by the system (e.g., by controlling the robotic controller) and/or by the user manually or via remote control of the one or more selected surgical devices. For example, a controller of the system may control a robotic controller to advance one or more of the surgical devices along a path defined by RP. The system may render a signal informing the user to advance the one or more selected surgical devices as may be desired.

With regard to the TAD, this distance may be determined by the user and/or system. For example, the TAD may be set by the user to 2 mm and stored in a memory of the system for further use. However, in yet other embodiments, the TAD may vary based upon a location of a distal end (e.g., tip or other portion) of the corresponding one or more surgical devices along the RP. Thus, when approaching an OOI along the RP, the TAD may decrease (e.g., to 1 mm) from an initial distance (e.g., 10 mm, etc.) or may be increased such that the one or more surgical devices such as the biopsy tool may be thrust from the natural pathway off-road to the OOI in one single advancement. Thus, the TAD may be set to a desired distance such as a distance of the ORP depending upon system settings.

Generally, it will be assumed that the bronchoscope (with or without the SSD tool) may be inserted within the natural pathway along the RP until a location at which a diameter of the natural pathway is less than or equal to the diameter of the bronchoscope. This distance may be specified by the RP. Thereafter, the SSD tool may be advanced to the OOI. Thus, a user may interface with the system to advance one or more of the one or more selected surgical implements such as the bronchoscope and/or the SSD tool along a path defined by the RP. After completing act 311, the system may continue to act 313.

During act 313, the system may determine a shape of one or more of the selected surgical devices. Accordingly, the system may query the SSD tool to obtain corresponding SSDI which may be processed to determine a shape thereof. Knowing the shape and the launch point, the system may determine a pose of the distal end of each of the one or more selected surgical devices. After completing act 313, the process may continue to act 315.

During act 315, the system may initially register the determined shape of the one or more selected surgical devices (e.g., determined from the SSDI) to the 3D volume. Assuming that the 3D volume is obtained using fluoroscopy methods, and the SSDI is obtained using a FORS-method, the system may then register the SSDI to the pre-operative 3D volume. The system may then form a virtual image of the one or more surgical devices (e.g., the bronchoscope and SSD tool in the present embodiments) in accordance with the determined shape and superimpose this virtual image upon the 3D volume to form a composite image. The composite image may thereafter be rendered on a rendering device of the system (e.g., see, FIGS. 4A through 5). The system may further distinguish each of the one or more surgical devices from each other such as by using different color highlighting. For example, the system may highlight the bronchoscope and the SSD tool using different colors. Each of the one or more surgical devices may be identified from the SSDI or via image analysis. Thus, an SSG may be distinguished readily from a SSBT, etc. Similarly, the system may distinguish the bronchoscope, a sheath, etc. using different colors, highlighting, etc. The system may further render instructions for the user such as instructions informing a user to advance one or more of the selected surgical devices along the RP by a TAD. After completing act 315, the system may continue to act 317.

During act 317, one or more of the one or more selected surgical devices (e.g., the bronchoscope and the SSD tool) may be advanced within the natural pathway as defined by, or substantially by, the RP as may be necessary. Accordingly, the one or more selected surgical devices may be advanced along the path in the airways of the lung (e.g., along the natural pathway defined by the RP). This advancement may be performed manually by a user or via remote control of one or more of the one or more selected surgical devices as may be desired. With regard to adjustment, the system may further adjust a shape or pose of the one or more selected surgical devices as may be necessary to confirm with the RP. For example, the system may control a uni-cath hub to rotate one or more of the one or more selected surgical devices such as the SSD tool and/or catheter. It is also envisioned that the system may determine and render instructions which may guide a user in adjusting one or more of the one or more selected surgical devices such as "rotate uni-cath hub +30 deg.," etc.

With regard to the advancement or adjustment of the selected surgical devices, for the sake of clarity, it will be assumed that each of the one or more selected surgical devices may be advanced in unison along the RP until it is determined to go off road, at which time the SSD tool may be advanced while the bronchoscope may not. However, the system may adjust each of the one or more selected surgical devices, in unison, independently, or substantially independently, of each other so that the path travelled by the one or more selected surgical devices may conform the RP to a desired fit. The RP may further include path segment information which may define one or more path segments for each of the one or more selected surgical devices such as the bronchoscope and the SSD tool. For example, the bronchoscope may travel along fewer path segments than the SSD tool. After completing act 317, the system may continue to act 319.

During act 319, the system may determine a shape of one or more of the selected surgical devices. Accordingly, the system may query a SSD of the UB and SSBT using any suitable method to obtain corresponding SSDI which may be processed to determine a shape thereof. This act may be similar to act 313. The determined shape may be considered a current or actual shape (real-time) of the one or more selected surgical devices. After completing act 319, the process may continue to act 321.

During act 321, the system may register the determined shape of the one or more selected surgical devices (e.g., determined from the SSDI) to each other and to the pre-operative 3D volume. This act may be similar to act 315. Similarly, the system may then render the registered determined shape of the one or more selected surgical devices superimposed upon the pre-operative 3D volume on a rendering device of the system and may output instructions to the user to advance one or more of the selected surgical devices, when the one or more surgical devices are advanced by a user. After completing act 321, the system may continue to act 323.

During act 323, the system may calculate error (e.g., deviation) between the RP and the current shape (e.g., a current path which is an actual path) of the one or more surgical devices using any suitable method. The process may do this using any suitable mathematical method or methods such as curve-fitting methods and the like. With regard to the error, continuous re-registration of shape to the pre-operative 3D volume will improve the further down the airways the bronchoscope advances because as the airways become smaller and smaller (e.g., decrease in diameter) they will approach the same size as the exterior of the bronchoscope thus restricting the freedom of movement of the bronchoscope and the SSD tool associated therewith. This restriction will lead to a closer fit between the detected shape and the shape of the RP. The system may stop advancement of the bronchoscope when its exterior dimensions approaches that of the inside of the airway in which it is traveling so as to prevent damage to the tissue of the airway. By continuously re-registering the shape to the pre-operative volume, error may be calculated between the RP and the current shape of the SSD in real time. As may be readily appreciated, it may be desirable to go off road prior when the airway becomes too small to navigate or prior to that position, such as when a shorter path to the OOI is provided. After completing this act, the system may continue to act 325.

During act 325, the system may form and render a GUI including the RP and the current shape of the one or more surgical devices superimposed upon the pre-operative 3D volume on a rendering device of the system. The system may further render an indication of the RP using any suitable method such as numerically or graphically. For example, the system may render those portions of the current shape that are determined to have the least error using green highlighting and those portions of the current shape that are determined to have the most error may be highlighted in red. Thus, the highlighting may change from green to red as the calculated error increases. Thus, the planned path and the current shape (e.g., actual path) may be superimposed (e.g., overlaid) upon the 3D volume and rendered with an indication of calculated error on a rendering device of the system such as on a display. However, in yet other embodiments, the calculated error may be rendered using a speaker or a haptic device where, for example, pitch and/or tone may increase as error increases and vice versa. After completing act 325, the system may continue to act 327.

In accordance with embodiments of the present system, acts 319 through 325 may be repeated continuously in real time over a desired time interval such as at least N respiratory cycles of the patient (where N is an integer that may be set by the user and/or system and may be equal to 1 in the following examples for the sake of clarity) so that the calculated error due to motion such as motion due to the respiratory cycle of a patient may be updated in real time.

During act 327, the system may determine whether to exit the natural pathway. Accordingly, in a case wherein it is determined to exit the natural pathway, the system may continue to act 329. However, in a case wherein it is determined not to exit the natural pathway, the system may repeat act 317.

In accordance with embodiments of the present system, the system may determine to exit the natural pathway when it is determined that the calculated error is less than a threshold error ($E_{thresh}$) However, the system may determine not to exit the natural pathway when it is determined that the calculated error is greater than or equal to the threshold error ($E_{thresh}$) By exiting the natural pathway, the SSD tool may be guided along an ORP to the OOI. In yet other embodiments, the system may determine to exit the natural pathway when it is determined that a tip (e.g., distal end) of the SSD tool or the bronchoscope is situated at that portion of the RP at which an exit through the airway wall is desired. In yet other embodiments, the system may determine to exit the natural pathway when a trajectory of the SSD tool intersects that of the OOI as is further discussed herein.

For example, as the lung operates as an elastic body, during inhalation and exhalation phases of a respiratory cycle, the lung may assume two very different states; expanded and collapsed states, respectively. However, it will be assumed that the OOI and the location of the exit in the wall of the natural pathway through which the SSD tool travels may be represented using rigid motion. This is more clearly illustrated with reference to FIG. 4A which shows a graphical depiction 400A of a 3D volume of a lung 463 having airways 453 during an exhalation phase generated in accordance with embodiments of the present system; and FIG. 4B which shows a graphical depiction 400B of a 3D volume of the lung of a patient having airways 453 during an inhalation phase generated in accordance with embodiments of the present system. As shown, an SSD tool is inserted within airways 453 and extends towards an OOI such as a lesion 455.

Figure 4A:
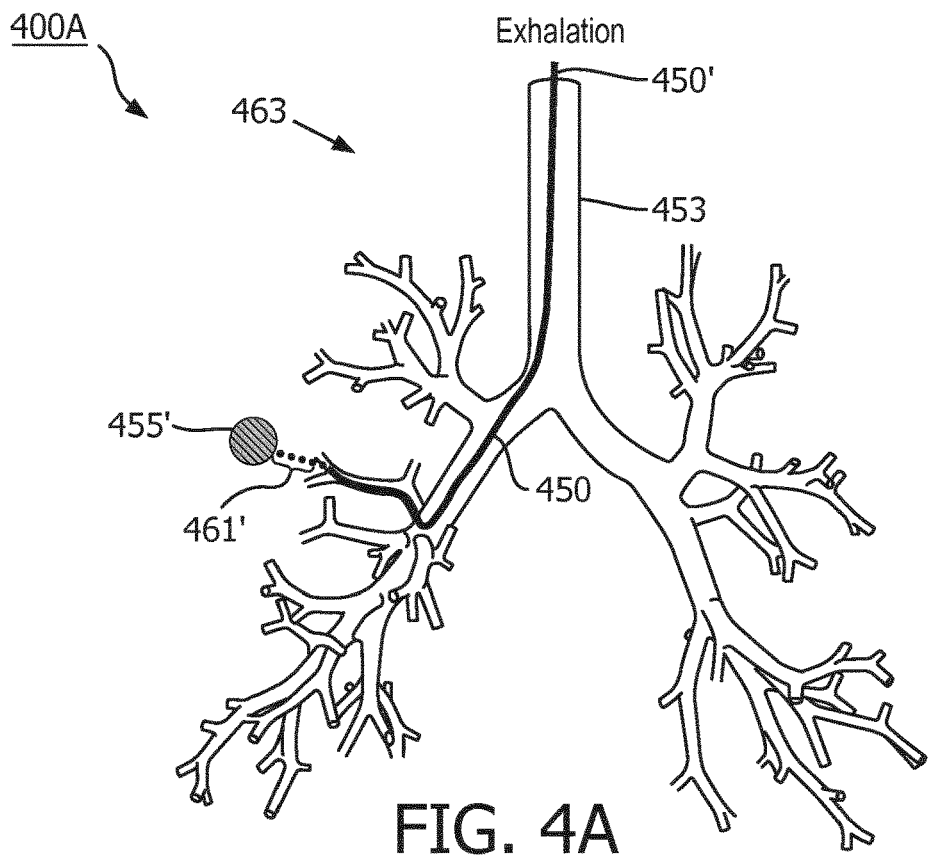
FIG. 4A shows a graphical depiction of a 3D volume of lungs having airways during an exhalation phase generated in accordance with embodiments of the present system.
Figure 4B:
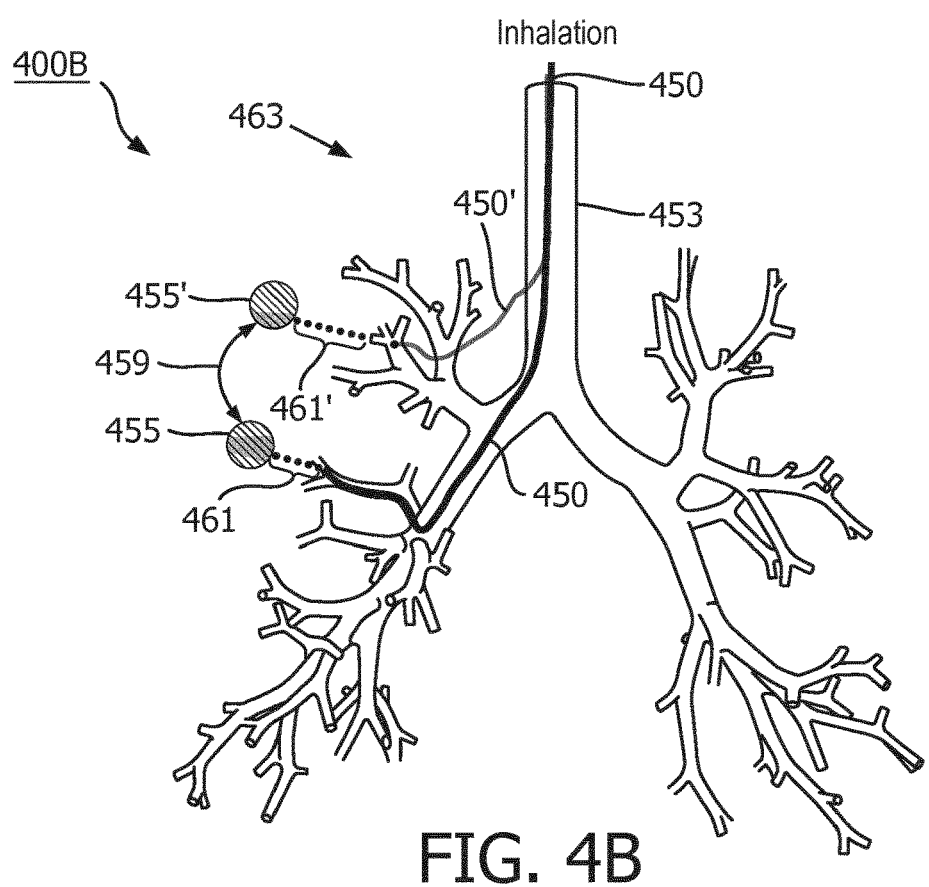
FIG. 4B shows a graphical depiction of a 3D volume of lungs of a patient having airways during an inhalation phase generated in accordance with embodiments of the present system.

With reference to FIG. 4B, the RP 450 is determined for a desired point in the respiratory cycle at which, for example, the lung 463 may be expanded the fullest and the airways 453 are expanded the most. This may ease passage of the one or more selected surgical implements such as the bronchoscope and the SSD tool within the natural pathway (e.g., airways of the lung 463) along the RP 450 towards the lesion 455. An ORP portion 461 of the RP 450 is shown as dotted lines 461 which portion may indicate a desired path of the SSD tool of the one or more selected surgical implements when it travels off road towards the lesion 455.

During the respiratory cycle, the lung 463 may expand and contract which may change the locations of portions of the lung 463, such as airways 453 and the lesion 455, in free space. This change may also change a shape of the one or more selected surgical devices that may be situated within the airways of the lung 463 which may have been assumed to have a shape which corresponds with the RP 450. For example, assuming that lung 463 in each of FIGS. 4A and 4B are shown in the same scale, the lung 463 during the exhalation portion of the respiratory cycle 'may shrink when compared to the size during the inhalation portion of the respiratory cycle. This change may result in a change of locations of portions of the lungs with reference to lesions and airways. For example, the lesion 455 may move to a location indicated by a virtual lesion 455' during the exhalation portion of the respiratory cycle. Similarly, the airways 453 may change their shape and size such that the RP 450 may shift to a virtual RP' 450' as shown. The motion of the lesion 455 may, thus, linearly move as illustrated by arrow 459. Accordingly, assuming the one or more selected surgical devices are situated along the RP 450 within the airways 453 of the lung 463, the shape and size as defined by an actual path may change during the respiratory cycle such that a more desirable path may correspond with the RP' 450' during the exhalation phase of the respiratory cycle. The RP' 450' at a time of inhalation may have a virtual ORP' 461' to the virtual lesion 455'. For the sake of clarity, only two discrete points in the respiratory cycle are discussed. However, other points may be selected throughout the respiratory cycle as desired such as when such point provides a more optimal path.

During a surgical intervention, at a given point (e.g., during the inhalation portion) in the respiratory cycle, a current path (e.g., an actual path) of an SSD tool should have substantially the same path (e.g., shape and size) as the RP during the same (or substantially the same) point in the respiratory cycle and, thus, the calculated error between the RP and the actual path at this point should be the lowest (of all calculated errors during all portions of the respiratory cycle). However, as the lungs change shape and size during the respiratory cycle, at about half a respiratory cycle from the point with the lowest error, the shape of the SSD tool should be different from the shape of the RP and the calculated error between the shape of the SSD tool and the RP may be expected to be about the greatest. Thus, with reference to the example, shown in FIG. 4B, the lowest error between the RP and the actual path is expected during the inhalation portion of the respiratory cycle and includes ORP 461.

For example, during a surgical intervention, an indication of the calculated error may be rendered in association with the shape of the surgical device (e.g., the SSD tool), the RP, and/or the 3D volume on a rendering device of the system in real time for the convenience of the user. Assuming the SSD tool is at an exit location, it may be determined (e.g., automatically by the system and/or user) to go off-road when the current path looks most like the RP and, thus, has the least error (or vice versa). At this point in time, it may be determined to exit the natural pathway. Thus, when the determined current path of the one or more selected surgical devices looks like the RP, the lungs are in a position (e.g., the inhalation phase) to advance the selected one or more surgical devices such as the SSBT. However, when the lungs are in the exhalation phase, the selected one or more surgical devices such as the SSBT should not be advanced to go off-road as the error at this time is expected to be substantially at a maximum value. Accordingly, the system may provide an indication of calculated error and render an indication of such on a rendering device of the system. For example, a display device, a haptic device situated in a control handle of the SSBT, and/or other rendering device may render the error. A physician may then be provided with an indication of the calculated error (e.g., using the displayed 3D image, haptic feedback such as vibrations that may be proportional to the calculated error during the respiratory cycle, etc.). In this way, when the error reaches its minimum value the physician may easily recognize such and may advance the SSBT to go off-road at that time.

Referring back to FIG. 3, during act 329, the one or more surgical devices may be advanced "off road" towards the OOI. The one or more surgical devices such as a biopsy device may be advanced manually by the surgeon or automatically by the system. For example, the system may control the robotic controller to advance the SSD tool (e.g., a selected one of the SSG or SSBT depending upon a selection of the system and/or user), automatically along the RP towards the OOI at the calculated time in the respiratory cycle that produces the calculated minimum error.

Figure 5:
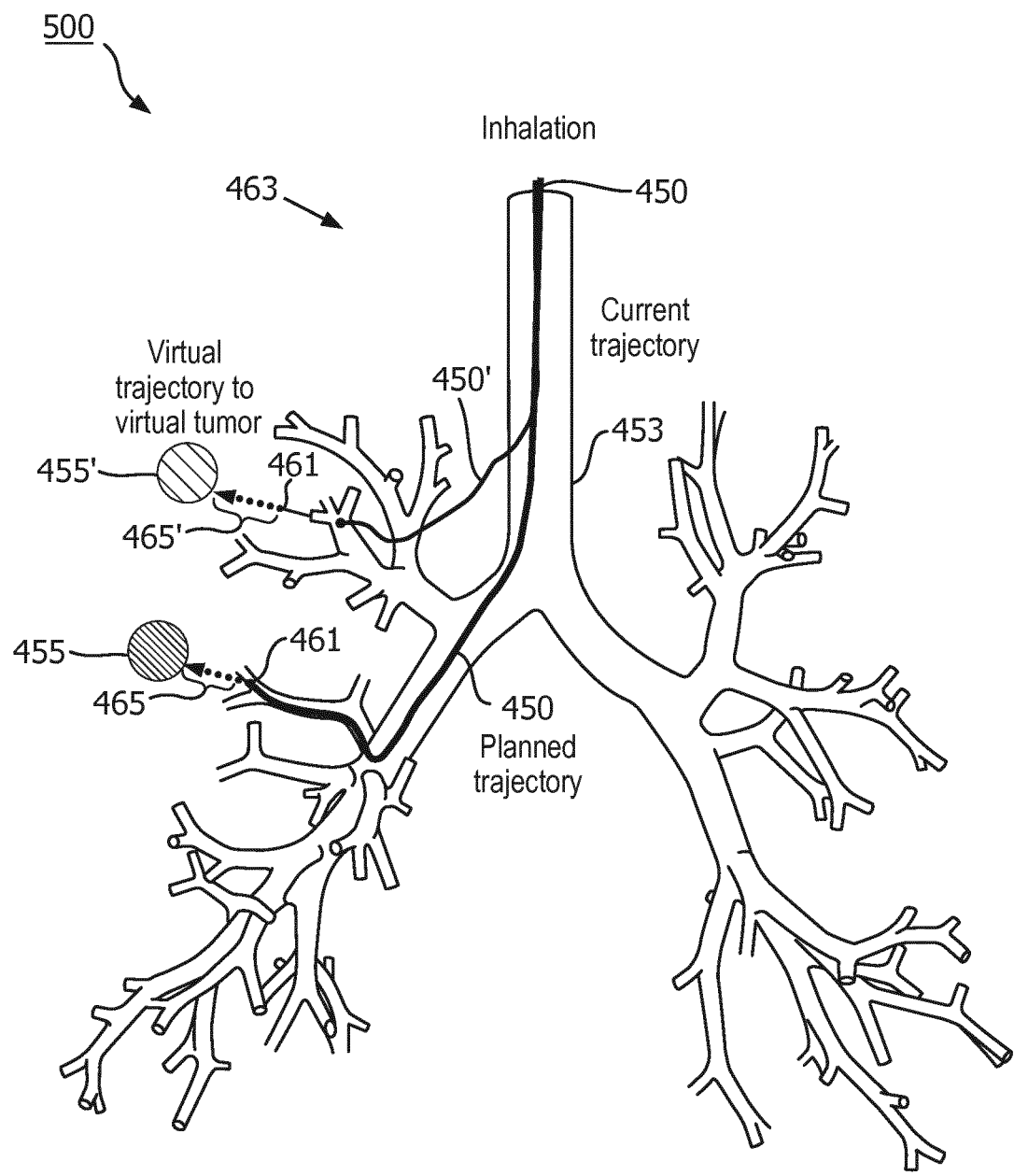
FIG. 5 shows a GUI 500 illustrating a detailed view of the 3D volume shown in FIG. 4B in accordance with embodiments of the present system.

In accordance with yet another method to off-road, it is envisioned that the RP may include information about the direction that the selected one or more surgical devices such as the SSD tool in the present embodiments should take (e.g., a trajectory) corresponding with the ORP of the RP upon exiting the natural pathway to reach the OOI. For example, FIG. 5 shows a GUI 500 illustrating a detailed view of the 3D volume shown in FIG. 4B in accordance with embodiments of the present system. The RP 450 may include the ORP portion 465 which may provide information about a direction the SSD tool should take upon exiting a corresponding airway 453 to reach the lesion 455 or virtual lesion 455' depending upon a time of the respiratory cycle. Since the tumor 454 substantially moves in unison with the adjacent airways 453 of the lung 463 during a full respiratory cycle (c.f., 455 and 455'), the direction the SSD tool should travel to reach the tumor 455 or virtual tumor 455' is not expected to substantially change during the respiratory cycle. Therefore, a proximal section of the SSD tool (e.g., that portion of the SSD tool that is within the natural pathway, e.g., excluding the distal tip) may be used to monitor the respiratory motion while the distal tip (e.g., the tip at the distal end) of the SSD tool may be positioned in the direction that it should be navigated off-road to reach the lesion 455 (or virtual lesion 455'). When the current trajectory of the SSD tool is overlaid on the 3D volume, a virtual trajectory 465' (which corresponds with the ORP 461' in the present embodiments) of the SSD tool may also be shown to the virtual tumor 455' (when the tip of the distal end of the SSD tool has reached the exit point). In these embodiments of the present system, the physician may then follow the virtual trajectory 465' to the tumor rather than waiting for an indication of the lowest calculated error between the current and planned trajectories. The system may determine the current trajectory of the SSD tool in accordance with the SSDI at or near the distal end of the SSD tool and render this information on the 3D volume as a current trajectory 465 or virtual trajectory 465' for the convenience of the user. For example, the system may determine the pose of the distal tip of the SSD tool and render a corresponding trajectory in real time such as the virtual trajectory 465'. Then, using this information, the user or the system may then guide the SSD tool off-road to the lesion 455 at any time without waiting for the indication of the lowest calculated error between the current and planned trajectories.

After completing act 329, the system may continue to act 331 where the system may perform a desired act on the OOI such as to obtain a biopsy of the lesion or to position an ablation device in the present embodiments. Thereafter, the system may store information generated and/or otherwise obtained during the current process in a memory of the system and/or render this information for the convenience of the user. Thereafter, the system may continue to act 333, where the process may end.

With regard to act 331, during this act the system may determine a path to an OOI using the natural pathways (e.g., without exiting and going off-road) and automatically guide one or more of the one or more selected surgical devices or render guidance information on a rendering device of the system such that a user may guide the one or more selected surgical devices to the OOI. Once the one or more selected surgical devices are situated at the OOI, the system may continue to act 329.

A benefit of the present system is that only a single 3D volume has to be obtained and a reference path determined. Thereafter, navigation information generated by the present system may be determined based upon the SSDI and the reference path. In accordance with embodiments of the present system, this may reduce patient exposure to radiation during an interventional procedure since for example, no additional fluoroscopic imaging is required.

Figure 6:
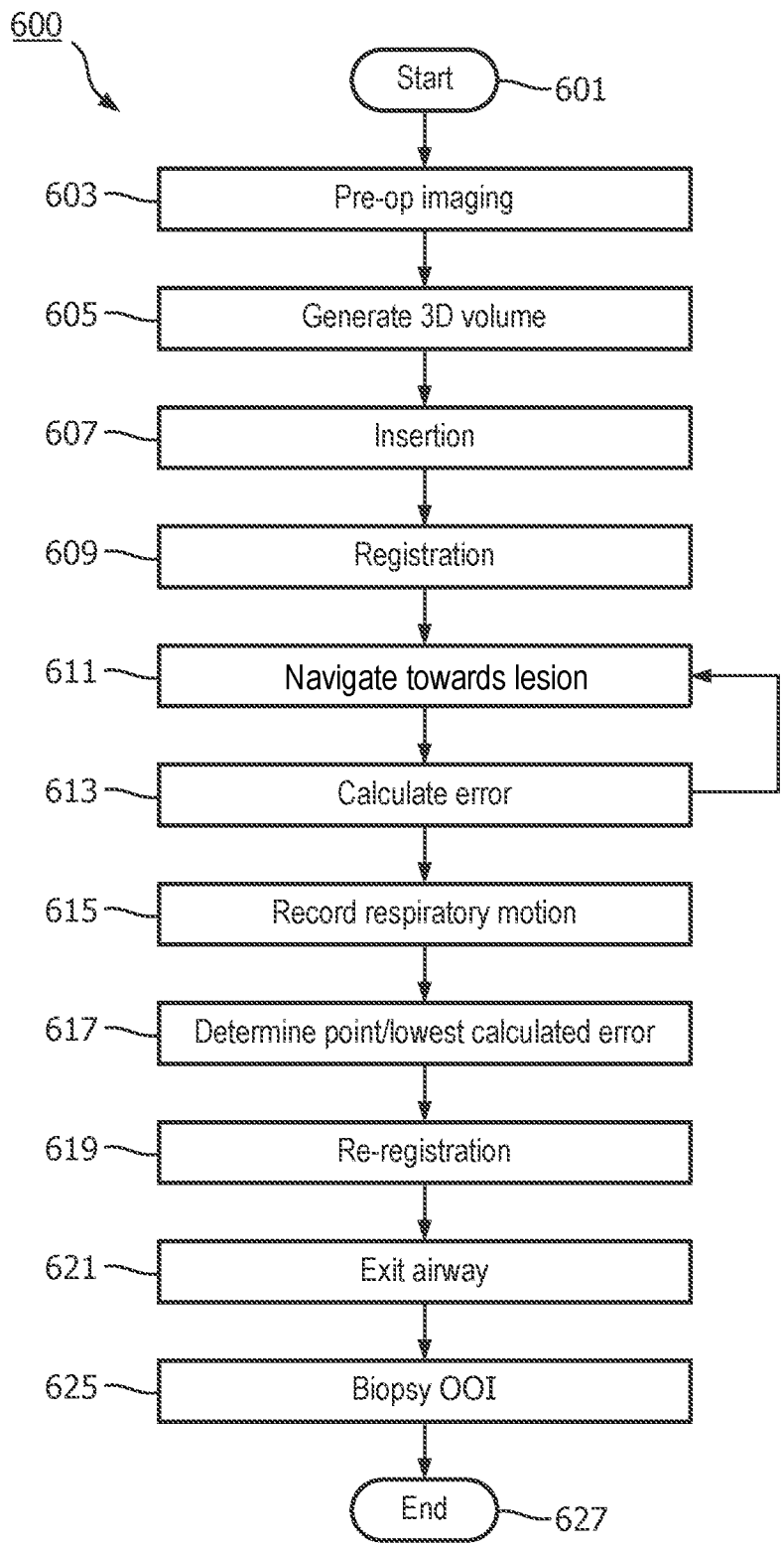
FIG. 6 shows a functional flow diagram performed by a process in accordance with embodiments of the present system.

FIG. 6 shows a functional flow diagram performed by a process 600 in accordance with embodiments of the present system. The process 600 may be performed using one or more processors, computers, controllers, etc., communicating over a network and may obtain information from, and/or store information to one or more memories which may be local and/or remote from each other. The process 600 may include one of more of the following acts. In accordance with embodiments of the present system, the acts of process 600 may be performed using one or more suitable coordinate registration systems operating in accordance with embodiments of the present system. Further, one or more of these acts may be combined and/or separated into sub-acts, as desired. Further, one or more of these acts may be skipped depending upon settings. For the sake of clarity, the process may be described with reference to a bronchoscope and SSD tool (e.g., a biopsy tool in the present embodiments) the latter of which may pass through a channel of the bronchoscope. However, without limitation, it should be understood that the process may employ a plurality of introducers each of which may include a separate or partially separate workflow. In operation, the process may start during act 601 and then proceed to act 603. Although the process 600 will be described with reference to a single lesion, portions of the process may be repeated for a plurality of lesions or other ROIs.

During act 603, the process may perform pre-operative imaging using an imaging method of the system such as a fluoroscopy image of a ROI such as the lungs of a patient. This act may be performed similarly to act 303. After completing act 603, the system may continue to act 605.

During act 605, the system may generate a 3D volume of the ROI and generate a reference path (RP) to a selected OOI within the 3D volume such as a lesion. The RP may include at least a portion within an airway of the lungs and an off-road portion. The RP may further set forth an exit area which may indicate an exit point at which an SSD tool may exit a wall of the airway to travel off-road. The RP may define a 3D path to the OOI. The OOI may be selected automatically by the system and/or by a user. After completing act 605, the system may continue to act 607.

During act 607, a bronchoscope is inserted and an SSD tool situated within a channel of the bronchoscope may be initially inserted within an airway of the lungs of the patient corresponding with the RP. In yet other embodiments the bronchoscope may include an SSD and/or the bronchoscope may be initially inserted without the SSD tool (e.g., up to the exit point) at which time the SSD tool may be inserted within a channel of the bronchoscope. After completing act 607, the system may continue to act 609. However, without limitation, it is also envisioned that the SSD tool may be inserted within the airway of the lungs without the bronchoscope as may be desired.

During act 609, the system may register SSDI with the pre-operative 3D volume so the SSD tool (and the associated bronchoscope) is registered with the pre-operative 3D volume (image). Accordingly, the system may obtain SSDI from the SSD tool using any suitable method such as a FORS method. Then, the system may register the SSDI with the pre-operative 3D volume so as to register the shape of the SSD tool and the associated bronchoscope with the pre-operative 3D volume. The system may then, in real time, render a virtual image of the shape of the SSD tool and the bronchoscope upon the pre-operative 3D volume. This act may be continuously performed during the process as desired thereby providing a real-time image of the SSD tool and/or the bronchoscope. After completing act 609, the system may continue to act 611.

During act 611, the bronchoscope and/or the SSD tool may be navigated towards the lesion either automatically by a controller of the system and/or by a user until it is determined for example that at least the tip of the SSD tool has reached the exit point (as defined by the RP). In accordance with embodiments of the present system, this process may occur discretely with the bronchoscope and SSD tool being advanced (together or independently of each other) by a threshold distance. After completing act 611, the process may continue to act 613.

During act 613, the system may calculate an error between the RP and the current path of the SSD tool. Accordingly, the system may obtain SSDI from the SSD tool and determine a current path of the SSD tool which may then be compared with the RP to calculate the error between the two (e.g., the RP and the current path). This error may be calculated using any suitable mathematical method such as a curve fitting model, etc. To limit extraneous data, the process may determine the error based upon selected portions of the RP and the current path. For example, the process may calculate error for only that portion of the SSD tool that is located within a natural pathway of the lungs, etc. as may be determined by the system and/or user. Once it is determined that the calculated error is less than a threshold error (e.g., for any given portion of the RP such as a portion of the RP that ends at the exit point and a portion of the SSD tool), it may be determined that a tip of the SSD tool (e.g., a distal end) is at the exit point and the process may continue to act 615. However, in a case wherein it is determined that the calculated error is greater than or equal to the threshold error, the process may repeat act 611.

Though not required, in accordance with embodiments of the present system re-registration of shape to the pre-operative volume may improve the further down the airways as the SSD tool advances because the airways become smaller and smaller and hence the SSD tool may only move inside the airway so much when it approaches the same size as the SSD tool itself. While re-registering (e.g., continuously), an error may be calculated between the RP and the current path of the bronchoscope. This information may be rendered to the physician along with an image of the current (actual) path of the bronchoscope and/or SSD tool (as determined by the SSDI) overlaid on the 3D volume and the RP. During exhalation and inhalation the lung is in two very different states (e.g., FIGS. 4A and 4B). At some point in the respiratory cycle, the current path will look like the planned path and have the lowest error. In accordance with embodiments of the present system, at this point in time a user may be prompted to (e.g., through the user interface) and/or a robotic system, may advance the bronchoscope and/or the SSD tool.

During act 615, the system may record respiratory motion for at least one full respiratory cycle. As readily appreciated, this operation may be performed continuously or during any portion of the process. Accordingly, the system may hold the SSD tool steady (e.g., by a user and/or robotic controller under the control of a controller of the system) and respiratory motion may be recorded for at least one respiratory cycle. Accordingly, the system may acquire SSDI in real time during this cycle and may then analyze the SSDI to determine respiratory motion during this at least one respiratory cycle. The shape of the SSDI may be determined at discrete points over the respiratory cycle such as every 100 msec during the at least one respiratory cycle. The respiratory motion may provide for a calibration of the system to determine a time to exit an airway and travel off-road to the lesion. After completing act 615, the process may continue to act 617.

During act 617, the process may determine a point in the respiratory cycle where the error is lowest. Accordingly, the system may calculate error between the RP and the current path of the SSD tool over the at least one respiratory cycle. The system may then determine a point in the at least one respiratory cycle in which the calculated error is lowest from the calculated errors. The error may be calculated at discrete points or for each time the SSDI was collected over the respiratory cycle such as every 100 msec. As the error may be expected to be lowest at that point in time during the respiratory cycle at which the shape of the SSD tool corresponds with the RP, this point may be referred to as the exit time point and may indicate a point in the respiratory cycle (e.g., with the lowest error) at which the bronchoscope and/or the SSD tool should exit the wall of the corresponding airway at the exit point. After completing act 617, the system may continue to act 619.

During act 619, the system may re-register after the bronchoscope and/or the SSD has reached the desired exit point and pose. After completing act 619, the system may continue to act 621. During act 621, the system may exit the airway. Accordingly, the system may await a corresponding time point in a current respiratory cycle that corresponds with the determined exit time point and may exit the wall of the airway to go off-roading at this point in time corresponding to the time in the respiratory cycle with the lowest error as discussed. Accordingly, if automatically controlling the SSD tool, the system may control the robotic controller to advance the SSD tool through the wall of the airway off-road towards the lesion at the time point in a current respiratory cycle that corresponds with the determined exit time point. However, the system may also provide for manual control of the SSD tool and may provide an indication of the time point in the respiratory cycle so that a user may guide the SSD tool to the lesion off-road at the time point in a current respiratory cycle that corresponds with the determined exit time point.

The system may also determine an angle (e.g., a desired pose) at which the SSD may exit the airway to travel off-road and may provide this information to the robotic controller and/or render this information for the convenience of the user. Thus, once the system knows at what time in the respiratory cycle the SSD should exit the airway and at what angle, the system may control the robotic controller to start navigation off-road at the desired time in the respiratory cycle and at a desired correct angle. Accordingly, the system may render a GUI to provide visual assistance or visual confirmation of the actions of the system for the convenience of the user.

Figure 7A:
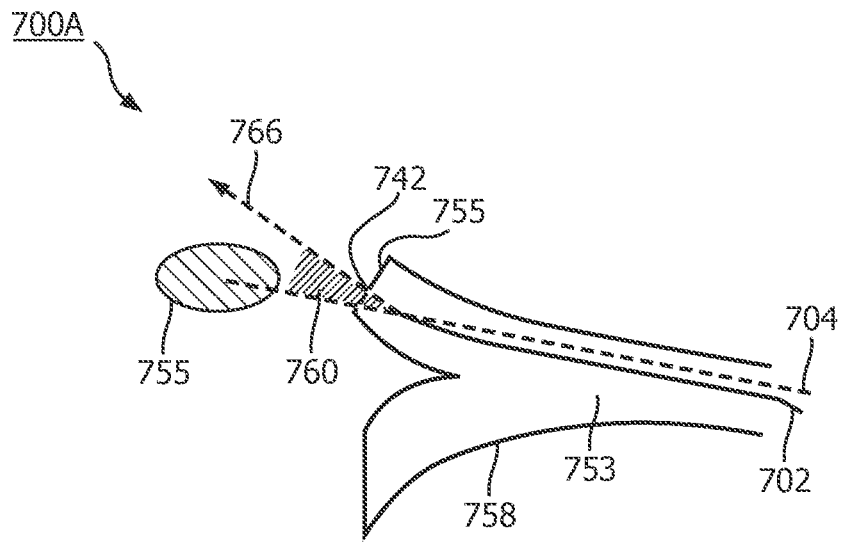
FIG. 7A shows a GUI including an indication of travel paths for guidance in accordance with embodiments of the present system.
Figure 7B:
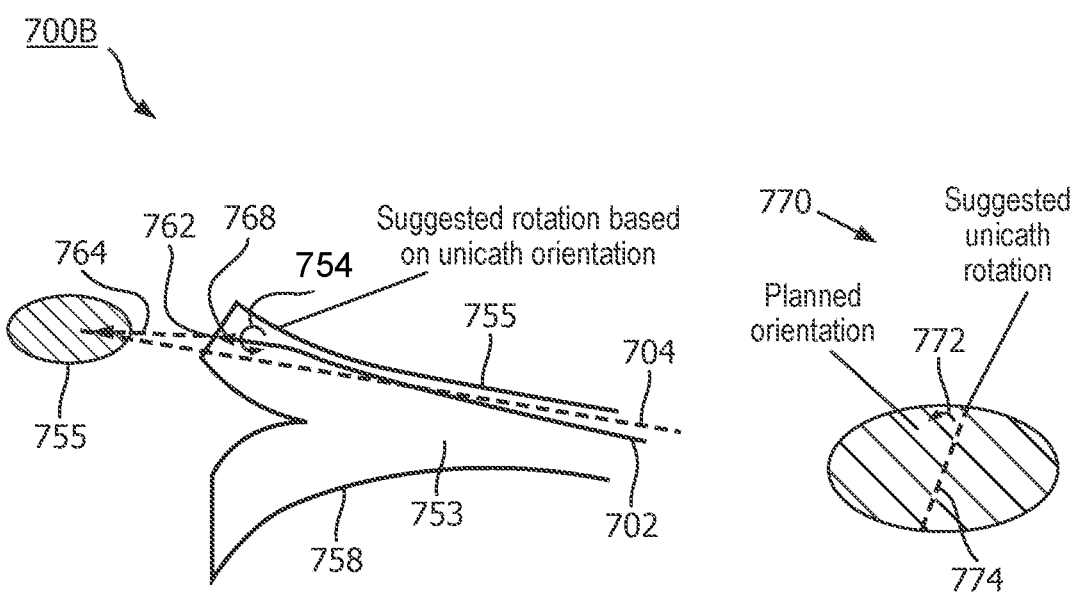
FIG. 7B shows a GUI including an indication of travel paths for guidance in accordance with embodiments of the present system.

In accordance with embodiments of the present system, the system may render a GUI that may provide a user with navigation assistance to aid a user when performing manual navigation. For example, the system may render a GUI that may provide information to assist the user in the alignment of the SSD tool relative to an OOI such as a lesion. This may be illustrated with respect to FIGS. 7A and 7B wherein FIG. 7A shows a GUI 700A including an indication of travel paths for guidance in accordance with embodiments of the present system; and FIG. 7B shows a GUI 700B including an indication of travel paths for guidance in accordance with embodiments of the present system.

With reference to the GUI 700A, the system may determine and render a current path 702 of a portion of the SSD tool (e.g., a current trajectory), an extrapolated trajectory 766 of the SSD tool, a RP 704 (e.g., a planned trajectory), an exit location 742, and an error indicator 760, which may be layered upon a corresponding portion of a 3D image volume (e.g., a pre-operative 3D image volume) and rendered on a rendering device of the system. The rendered 3D image volume may include a virtual image of the airways 753, airway walls 758, and a tumor 755. The error indicator 760 may be rendered using any suitable method and may indicate the error between the current path 702 and the RP 704. For example, the error indicator 760 may be represented as a highlighted area between the current path 702 and the RP 704 with an area which increases as error increases and decreases with as error decreases. The exit location 742 may vary in accordance with the extrapolated trajectory 766 of the SSD tool and its intersection with an airway wall 758.

With reference to the GUI 700B, the system may further determine a dynamic trajectory 764 which may be dynamically extrapolated based upon the SSDI such as SSDI which may be indicative of a pose of a distal end 768 of the SSD tool as determined from the SSDI and updated in real time. As the pose and/or shape of the SSD tool changes during the breathing cycle, the system may update the dynamic trajectory 764 accordingly. The system may further provide an indication of an exit location 762 based upon the dynamic trajectory 764 and its intersection with an airway wall 758. The system may further determine suggested rotation information and render a graphical depiction of this using any suitable method such as a rotational arrow 754 which may be indicative of the suggested rotation of the SSD tool which may be performed by, for example, rotating a uni-cath hub to which the SSD tool is coupled. The suggested rotational information may further be rendered using a rotational guide 770 which may provide a suggested rotational vector 772 indicative of a suggested rotation of a uni-cath such that the SSD tool may move from a current location shown as dotted line 774 to a planned orientation as shown.

The dynamic trajectory and the suggested rotation information may provide a user with an indication that may suggest the repositioning necessary to achieve the desired trajectory both linearly and rotationally. If the distal portion of the distal end of the SSD tool (e.g., which may include a needle in the present example) takes a curved path, it may be possible for some repositioning to be achieved by rotating the tool at its proximal end. As the relation between the pose of the proximal and distal end of the bronchoscope and/or SSD is known a-priori and the presence of such a curvature is detectable by shape sensing, the uni-cath may track the proximal rotation of the tool, so that an overlaid display between distal and proximal orientation may be presented.

Referring back to FIG. 6, after completing act 621, the system may continue to act 625. During act 625, the tool may be controlled (manually or automatically) to biopsy the lesion using any suitable desired method. For example, the tool may be controlled to obtain a tissue sample from the lesion. After completing act 625, the process may continue to act 627 where the process may end.

Figure 8:
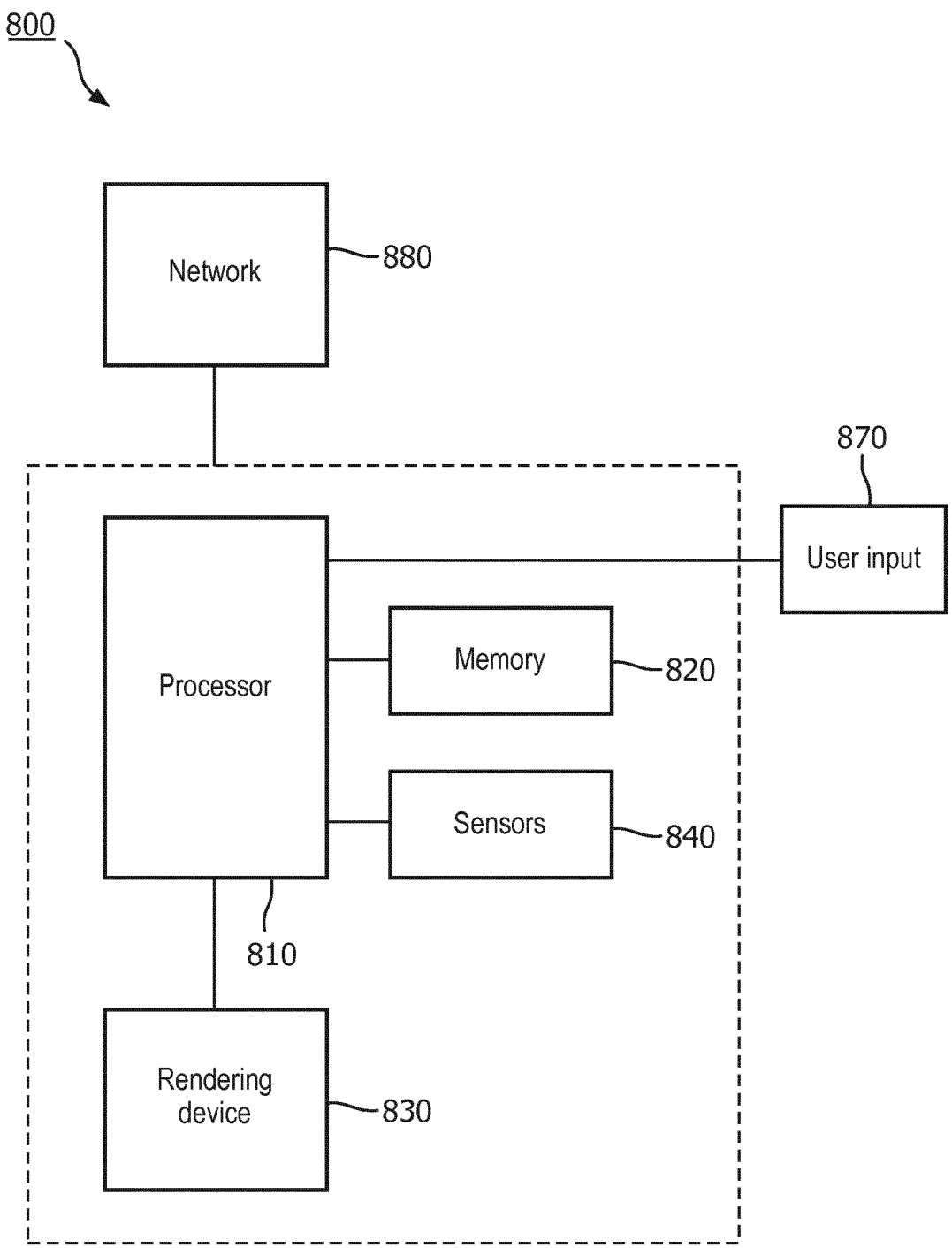
FIG. 8 shows a portion of a system in accordance with embodiments of the present system.

FIG. 8 shows a portion of a system 800 in accordance with embodiments of the present system. For example, a portion of the present system may include a processor 810 (e.g., a controller such as the controller 122 shown in FIG. 1) operationally coupled to a memory 820, a user interface (UI) including a rendering device such as a display 830, sensors 840, a communication network 880 and a user input device 870. The memory 820 may be any type of device for storing application data as well as other data related to the described operation. The application data and other data are received by the processor 810 for configuring (e.g., programming) the processor 810 to perform operation acts in accordance with the present system. The processor 810 so configured becomes a special purpose machine particularly suited for performing in accordance with embodiments of the present system.

The operation acts may include configuring a system including for example, an SSD tracking system (e.g., sensors 840) in accordance with system settings. For example, the processor 810 may determine a RP to an OOI and obtain SSDI from an SSD along the RP. The processor 810, thereof may process received signals such as sensor information, SSD information, etc., and transform these signals to determine a shape of an SSD as well as pose of the tip of the SSD and one or more associated medical devices, and may generate content which may include image information (e.g., still or video images), data, and/or graphs that may be rendered on, for example, a UI of the system such as on the display 830, a speaker, etc. The content may include image information as may be generated by a medical imaging system of the present system and/or may include guidance information (e.g., move right, left, arrows, etc.) to guide a user during a procedure. Further, the content may then be stored in a memory of the system such as the memory 820 and/or on another device such as on a device coupled to the processor 810 through the network 880 for later use. The processor 810 may further register a location of the SSD and/or the associated medical device and/or fuse the content obtained from the SSD (e.g., shape information) with information obtained from other medical imaging systems such as a fluoroscopy imager, MRI and/or computer-aided tomography (CAT), X-ray, etc. Thus, operation acts may include acquiring, providing, and/or rendering of content such as a 3D image volume. The processor 810 may render the content such as image information on a UI of the system such as on the rendering device 830 (e.g., a display) of the system.

The user input 870 may include a keyboard, a mouse, a trackball, or other device, such as a touch-sensitive display, which may be stand alone or part of a system, such as part of a personal computer, a personal digital assistant (PDA), a mobile phone (e.g., a smart phone), a monitor, a smart or dumb terminal or other device for communicating with the processor 810 via any operable link such as a wired and/or wireless communication link. The user input device 870 may be operable for interacting with the processor 810 including enabling interaction within a UI as described herein. Clearly the processor 810, the memory 820, display 830, and/or user input device 870 may all or partly be a portion of a computer system or other device such as a client and/or server.

The methods of the present system are particularly suited to be carried out by a computer software program, such program containing modules corresponding to one or more of the individual steps or acts described and/or envisioned by the present system. Such program may of course be embodied in a computer-readable medium, such as an integrated chip, a peripheral device or memory, such as the memory 820 or other memory coupled to the processor 810.

The program and/or program portions contained in the memory 820 may configure the processor 810 to implement the methods, operational acts, and functions disclosed herein. The memories may be distributed, for example between the clients and/or servers, or local, and the processor 810, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 810. With this definition, information accessible through a network is still within the memory, for instance, because the processor 810 may retrieve the information from the network for operation in accordance with the present system.

The processor 810 is operable for providing control signals and/or performing operations in response to input signals from the user input device 870 as well as in response to other devices of a network and executing instructions stored in the memory 820. The processor 810 may include one or more of a microprocessor, an application-specific or general-use integrated circuit(s), a logic device, etc. Further, the processor 810 may be a dedicated processor for performing in accordance with the present system or may be a general-purpose processor wherein only one of many functions operates for performing in accordance with the present system. The processor 810 may operate utilizing a program portion, multiple program segments, or may be a hardware device utilizing a dedicated or multi-purpose integrated circuit.

Embodiments of the present system may provide imaging methods to acquire and/or reconstruct images. However, without limitation it should be understood that embodiments of the present system may further include imaging systems such as MRI, computer-aided tomography (CT), optical, X-ray, and/or combinations thereof. Further, embodiments of the present system may be ideally suited for surgical interventional techniques which may generate and render image and/or sensor information from one or more imaging systems (e.g., ultrasound, CT scans, MRI, X-ray etc.) having different coordinate systems in real-time with a unified coordinate system. The system may determine a pose of an interventional device and may register the device and/or image information obtained from the device with these other systems. Accordingly, the system may determine velocity and/or pose of the interventional device for registration with these other systems.

Accordingly, embodiments of the present system may employ shape-sensing methods such as OSS methods to determine position and orientation of medical devices (e.g., which may include medical tools such as biopsy tools) within a patient in real time and may generate corresponding position information (e.g., in 2D or 3D) indicative of position and orientation of the medical device within the patient. The position information may be registered to other acquired information such as may be acquired using EM tracking, X-Ray, fluoroscopy, MRI, ultrasound, CT and/or the like. For example, the system may determine the position of one or more medical devices within natural pathways of a patient (e.g., lung airways) and form corresponding position information. Then, a path of the medical device may be determined in accordance with the position information and compared to one or more pre-planned paths as may be determined from baseline imaging such as pre-operative images and/or the like which may obtained using suitable medical imaging methods.

Accordingly, embodiments of the present system may generate real-time guidance information in the presence of respiratory/cardiac motion for navigation of flexible devices in the lung based upon the real-time position information. Error deviation of the current path from the planned path may be used to help time the navigation both inside and outside (off-road) of the airways or other natural pathways of an object under observation such as a patient. This may provide a system and method for determining when to exit a natural pathway such as an airway and begin navigating off-road within an object under observation such as patient in real time.

Although embodiments of the present system are described with respect to lung biopsy procedures, without limitation, it should be understood that embodiments of the present system may be operative with various other applications such as pulmonology applications including surgical excision or ablation of tissue. It is further envisioned that applications of the present system may be applied to other applications such as cardiac, vascular (crossing a CTO, repairing vessels, etc.) and/or gastrointestinal-tract applications and/or the like.

Thus, embodiments of the present system may provide systems and methods for trajectory planning when a lesion is not attached to the airway and/or when the device must otherwise be used off-road, all while taking into account real time respiratory and cardiac motion. Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, any section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated;

i) the term "plurality of" an element includes two or more of the claimed element, and does not imply any particular range of number of elements; that is, a plurality of elements may be as few as two elements, and may include an immeasurable number of elements; and j) the term and/or and formatives thereof should be understood to mean that only one or more of the listed elements may need to be suitably present in the system in accordance with the claims recitation and in accordance with one or more embodiments of the present system.

What is claimed is:

1. A medical navigation system, comprising:
   a shape-sensing device (SSD) configured to generate SSD information (SSDI) indicating at least a shape of the SSD along a length of the SSD; and
   a controller configured to:
      generate a three-dimensional (3D) volume based upon image information of a region of interest (ROI) generated by an imager;
      determine a reference path (RP) to an object-of-interest (OOI) situated within the ROI, the RP defining an on-road path (ONP) through at least one natural pathway of an organ that moves due to cyclical motion of a patient and an adjacent off-road path (ORP) through tissue of the organ leading to the OOI, and an exit point through the at least one natural pathway of the organ, the exit point being situated between the ONP and the ORP;
      query the SSD to obtain the SSDI when the SSD is situated within the at least one natural pathway and is moving due to the cyclical motion;
      determine the shape and a pose of the SSD based upon the SSDI obtained when the SSD is situated within the at least one natural pathway and is moving due to the cyclical motion;
      determine a deviation between the RP and the shape and the pose of the SSD, as determined; and
      determine when to exit a wall of the at least one natural pathway and begin the ORP based upon the determined deviation and the cyclical motion of the patient.

2. The medical navigation system of claim 1, wherein the controller is further configured to render a graphical user interface (GUI) with the RP and the determined shape of the SSD superimposed upon the 3D volume and an indication of the determined deviation.

3. The medical navigation system of claim 1, wherein the controller is further configured to determine when the determined deviation is at a minimum value, and wherein when it is determined that the determined deviation is at the minimum value, the controller is further configured to render an indication to begin the ORP.

4. The medical navigation system of claim 1, wherein when a distal tip of the SSD is determined to be substantially located at an end of the ONP, the controller is further configured to query the SSD to acquire the SSDI and determine a pose of the distal tip of the SSD.

5. The medical navigation system of claim 1, wherein the controller is further configured to determine an expected trajectory of the distal tip of the SSD through the ORP based upon the determined pose of the distal tip of the SSD.

6. The medical navigation system of claim 1, wherein the controller is further configured to determine an angular error between an expected trajectory of a distal tip of the SSD and the RP for the ORP and to render the determined angular error when the distal tip of the SSD is determined to be substantially located at an end the ONP.

7. The medical navigation system of claim 1, further comprising at least one robotic controller configured to control motion of the SSD in accordance with navigation information generated by the controller.

8. A method of navigating a shape-sensing device (SSD) the method comprising:
   generating a three-dimensional (3D) volume based upon image information of a region of interest (ROI) acquired by an imager;
   determining a reference path (RP) to an object-of-interest (OOI) situated within the ROI, the RP defining an on-road path (ONP) through at least one natural pathway of an organ subject to cyclical motion and an adjacent off-road path (ORP) through tissue of the organ leading to the OOI, and an exit point situated between the ONP and the ORP;
   querying the SSD to obtain SSD information (SSDI), generated by the SSD to indicate at least a shape of the SSD along a length of the SSD, when the SSD is situated within the at least one natural pathway and is subject to the cyclical motion;
   determining the shape and a pose of the SSD based upon the SSDI obtained when the SSD is situated within the at least one natural pathway and is subject to the cyclical motion;
   determining a deviation between the RP and the shape and the pose of the SSD, as determined; and
   determining when to exit a wall of the at least one natural pathway and begin the ORP based upon the determined deviation and the cyclical motion.

9. The method of claim 8, further comprising:
   rendering a graphical user interface (GUI) with the RP and the determined shape of the SSD superimposed upon the 3D volume and an indication of the determined deviation.

10. The method of claim 8, further comprising:
    determining when the determined deviation is a calculated error and when the calculated error is at a minimum value.

11. The method of claim 10, further comprising:
rendering an indication to begin the ORP when it is determined that the calculated error is at the minimum value.

12. The method of claim 8, further comprising:
determining a pose of a distal tip of the SSD using the SSDI generated by the SSD; when the distal tip of the SSD is determined to be substantially located at an end the ONP.

13. The method of claim 12, further comprising:
determining an expected trajectory of the distal tip of the SSD through the ORP based upon the determined pose of the distal tip of the SSD.

14. The method of claim 8, further comprising:
determining an angular error between an expected trajectory of a distal tip of the SSD and the RP for the ORP; and
rendering the determined angular error when the distal tip of the SSD is determined to be substantially located at an end of the ONP.

15. A non-transitory computer readable medium storing computer instructions that, when executed by a processor, configure the processor to:
generate a three-dimensional (3D) volume based upon image information of a region of interest (ROI) acquired by an imager;
determine a reference path (RP) to an object-of-interest (OOI) situated within the ROI, the RP defining an on-road path (ONP) through at least one natural pathway of an organ that moves due to cyclical motion of a patient and an adjacent off-road path (ORP) through tissue of the organ leading to the OOI, and an exit point through the at least one natural pathway of the organ, the exit point being situated between the ONP and the ORP;
query a shape-sensing device (SSD) to obtain SSD information (SSDI), generated by the SSD for indicating at least a shape of the SSD along a length of the SSD, when the SSD is situated within the at least one natural pathway and is moving due to the cyclical motion;
determine the shape and a pose of the SSD based upon the SSDI obtained when the SSD is situated within the at least one natural pathway and is moving due to the cyclical motion;
determine a deviation between the RP and the shape and the pose of the SSD, as determined; and
determine when to exit a wall of the at least one natural pathway and begin the ORP based upon the determined deviation and the cyclical motion.

16. The non-transitory computer readable medium of claim 15, wherein the computer instructions further configure the processor render a graphical user interface (GUI with the RP and the determined shape of the SSD superimposed upon the 3D volume and an indication of the determined deviation.

17. The non-transitory computer readable medium of claim 15, wherein the computer instructions further configure the processor:
determine when the determined deviation is at a minimum value; and
render an indication to begin the ORP when it is determined that the determined deviation is at the minimum value.

18. The non-transitory computer readable medium of claim 15, wherein the computer instructions further configure the processor to query the SSD to acquire the SSDI and determine a pose of a distal tip of the SSD, when the distal tip of the SSD is determined to be substantially located at an end the ONP.

* * * * *